(12) United States Patent
Pande et al.

(10) Patent No.: US 8,362,250 B2
(45) Date of Patent: Jan. 29, 2013

(54) FLUORESCENT DYES AND COMPOUNDS, METHODS AND KITS USEFUL FOR IDENTIFYING SPECIFIC ORGANELLES AND REGIONS IN CELLS OF INTEREST

(75) Inventors: Praveen Pande, Holbrook, NY (US); Hilary J. Cox, Centerport, NY (US); Yuejun Xiang, Bayside, NY (US); Wayne Forrest Patton, Dix Hills, NY (US)

(73) Assignee: Enzo Biochem, Inc., Farmingdale, NY (US)

( * ) Notice: Subject to any disclaimer, the term of this patent is extended or adjusted under 35 U.S.C. 154(b) by 509 days.

(21) Appl. No.: 12/586,386

(22) Filed: Sep. 21, 2009

(65) Prior Publication Data
US 2010/0068752 A1 Mar. 18, 2010

Related U.S. Application Data

(63) Continuation-in-part of application No. 12/315,629, filed on Dec. 4, 2008, which is a continuation-in-part of application No. PCT/US2007/016581, filed on Jul. 24, 2007, which is a continuation-in-part of application No. 11/177,923, filed on Jul. 7, 2003, now Pat. No. 7,737,281, which is a continuation-in-part of application No. 11/137,771, filed on May 24, 2005, now Pat. No. 7,569,695.

(51) Int. Cl.
*C07F 9/28* (2006.01)
*C12Q 1/00* (2006.01)

(52) U.S. Cl. ............... 546/23; 435/4; 546/22; 544/128; 544/337; 436/103

(58) Field of Classification Search ............... 546/23, 546/22; 544/128, 337; 435/4; 436/103
See application file for complete search history.

(56) References Cited

PUBLICATIONS

Morotti, T. et al.: Zirconium phosphate/phosphonate multilayered films based on push-pull stilbazolium salt: synthesis, characterization and second harmonic generation. Dalton Trans., vol. 22, pp. 2974-2982, 2008.*

* cited by examiner

*Primary Examiner* — Charanjit Aulakh
(74) *Attorney, Agent, or Firm* — Elie Gendloff, Esq.

(57) ABSTRACT

The present invention provides dyes and labeled reagents that may be used in the detection or quantification of desirable target molecules, such as proteins, nucleic acids and cellular organelles. Dyes are provided that may be used free in solution where the binding of the dye to the target molecule provides signal generation. Dyes provided in this invention can comprise reactive groups that may be used to attach the dyes to probes that will bind to desirable target molecules. The novel dyes of the present invention have been substituted with specific groups to provide beneficial properties.

33 Claims, 11 Drawing Sheets

CELLS STAINED WITH DYE 1

BRIGHT FIELD

GREEN CHANNEL

CELLS STAINED WITH DYE 2

BRIGHT FIELD

GREEN CHANNEL

CELLS STAINED WITH DYE 4

BRIGHT FIELD

ORANGE CHANNEL

CELLS STAINED WITH DYE 5

BRIGHT FIELD

RED CHANNEL

CELLS STAINED WITH DYE 6

BRIGHT FIELD

RED CHANNEL

CELLS STAINED WITH DYE 7

BRIGHT FIELD

ORANGE CHANNEL

CELLS STAINED WITH DYE 8

BRIGHT FIELD

Cy5 CHANNEL

CELLS STAINED WITH DYE 9

BRIGHT FIELD

RED CHANNEL

CELLS STAINED WITH DYE 10

BRIGHT FIELD

ORANGE CHANNEL

CELLS STAINED WITH DYE 10

BRIGHT FIELD

GREEN CHANNEL

CELLS STAINED WITH DYE 12

BRIGHT FIELD

RED CHANNEL

FLUORESCENT DYES AND COMPOUNDS, METHODS AND KITS USEFUL FOR IDENTIFYING SPECIFIC ORGANELLES AND REGIONS IN CELLS OF INTEREST

RELATED APPLICATIONS

This application is a continuation-in-part of U.S. patent application Ser. No. 12/315,629, filed Dec. 4, 2008, which is a continuation-in-part of PCT/US2007/016581, filed Jul. 24, 2007, which is a continuation-in-part of U.S. patent application Ser. No. 11/177,923, filed Jul. 7, 2003, now U.S. Pat. No. 7,737,281 which is a continuation-in-part of U.S. patent application Ser. No. 11/137,771, filed May 24, 2005, now U.S. Pat. No. 7,569,695 B2, issued on Aug. 4, 2009.

FIELD OF THE INVENTION

This invention relates to methods and kits for identifying specific organelles or regions in cells of interest. This invention also relates to fluorescent dyes and fluorescent compounds useful for identifying organelles in live and dead cells, including nuclei and organelles other than nuclei (non-nuclear organelles). More particularly, this invention relates to the identification of subcellular organelles, cell domains, cell regions, and the like, within living cells or extracellularly, with the identifying fluorescent dye or fluorescent compound retained within or otherwise localized to the specific subcellular organelles, cell domains or cells regions.

All patents, patent applications, patent publications, scientific articles and the like, cited or identified in this application are hereby incorporated by reference in their entirety in order to describe more fully the state of the art to which the present invention pertains.

BACKGROUND OF THE INVENTION

Cell-based assays are increasingly gaining in popularity in the pharmaceutical industry due to their high physiological relevance. Among the advantages of these assays are their ability to predict compound usefulness, evaluate molecular interactions, identify toxicity, distinguish cell type-specific drug effects, and determine drug penetration. Cell-based assays are relevant throughout the drug discovery pipeline because they are capable of providing data from target characterization and validation leading to identification (primary and secondary screening) to terminal stages of toxicology. Current industry trends of performing drug screening with cell context demand easily monitored, non-invasive reporters. Fluorescent proteins fulfill this demand more completely than any other available tools and have demonstrated applicability and versatility as molecular and cellular probes in life sciences and biomedical research. Among patents relating to fluorescent protein technology are U.S. Pat. Nos. 5,491,084; 5,625,048; 5,777,079; 5,804,387; 5,968,738; 5,994,077; 6,027,881; 6,054,321; 6,066,476; 6,077,707; 6,124,128; 6090,919; 6,172,188; 6,146,826; 6,969,597; 7,150,979; 7,157,565; 7,166,444; 7,183,399 and 7,297,782, all incorporated by reference in their entirety.

Requirements for advanced screening assays are driven by the objective of identifying candidate compounds which fail early in the drug discovery pipeline. This fundamental approach increases efficiency, reduces costs, and results in shorter time to market for new drugs. In order to fail compounds early, however, information-rich data for accurate early-stage decision making is required. Such data may be derived by screening compounds in context, that is, by screening in relevant living systems, rather than with classical biochemical assays. To do so, sophisticated imaging platforms, such as high-content screening (HCS) workstations, must often be incorporated. The industrialization of fluorescent microscopy has led to the development of these high-throughput imaging platforms capable of HCS. When coupled with fluorescent protein reporter technology, HCS has provided information-rich drug screens, as well as access to novel types of drug targets.

As industry trends advance toward analysis in living systems (e.g., cells, tissues, and whole organisms), fluorescent proteins, by virtue of their non-invasive, non-destructive properties, are becoming indispensable tools for live-cell analysis. A broad range of fluorescent protein genetic variants are now available, with fluorescence emission profiles spanning nearly the entire visible light spectrum. Mutagenesis efforts in the original jellyfish *Aequorea victoria* green fluorescent protein have resulted in new fluorescent probes that range in color from blue to yellow and these are some of the most widely used in vivo reporter molecules in biological research today. Longer wavelength fluorescent proteins which emit in the orange and red spectral regions, have been developed from the marine anemone *Discosoma striata* and reef corals belonging to the class *Anthozoa*. Other species have also been mined to produce similar proteins having cyan, green, yellow, orange, red, and even far-red fluorescence emission.

Recent emphasis on multi-color imaging in HCS has created renewed demand for easily measured, non-invasive, and non-disruptive cellular and molecular probes. With the increasingly expanded repertoire of fluorescent proteins has come increased demand for complementary reagents, such as organic fluorochrome counter-stains that augment analysis by providing information relating to co-localization of the fluorescent proteins to various organelles and subcellular targets. To date, however, concerted efforts in developing such organic fluorochromes specifically tailored to working in concert with fluorescent proteins, has been limited in scope. The application of fluorescent proteins and organic fluorochromes is not an "either-or" proposition. Each technology has distinct advantages and limitations. These two technologies can be optimized and combined to work in concert, however, in order to maximize the information content obtained from fluorescence microscopy and imaging-based screening approaches. By doing so, achieving rich multi-dimensional physiological information can be obtained.

While suitable for analysis of cell surfaces and permeabilized cells, fluorescently-labeled antibodies have few practical applications for intracellular imaging in living cells. The limited application of fluorescent antibodies stems from due their inherent inability to penetrate their targets. This has given rise to development of cell-permeable small molecule organic fluorochromes, certain ones of which naturally sequester inside-specific organelles, based upon biophysical or biochemical properties favoring that distribution. Acceptable small molecule organic probes for cell imaging and analysis need to be minimally perturbing, versatile, stable, easy-to-use, and easy to detect using non-invasive imaging equipment. A problem with the classical organic probes from histology past is that many of them either require cofactors or fixation and staining, the latter only reporting on the static condition of a dead cell. The required additional steps may be time consuming, expensive and in the case of fixing and staining, lack biological relevance. In the context of the analyses described above, an organic probe must be able to report upon events in living cells and in real time. Simplicity is of key importance, especially in the context of drug screening.

While various organic fluorochromes have been developed in the past for live cell analysis, typically they were not devised with optimization of performance in conjunction with the wide palette of available fluorescent proteins in mind. For instance, several disclosures (U.S. Pat. Nos. 5,338,854; 5,459,268; 5,686,261; 5,869,689; 6,004,536; 6,140,500 and 6,291,203 B1, as well as US Patent Publications Nos. 2005/0054006 and 2007/0111251 A1, references incorporated herein) disclose organic fluorochromes which are described as useful for visualizing membranes, mitochondria, nuclei and/or acidic organelles. Additional examples of various fluorochromes and their application in biological imaging may be found in the published literature (see, for example, Pagano et al, 1989; Pagano et al, 1991; Deng et al, 1995; Poot et al, 1996; Diwu et al, 1999; Rutledge et al, 2000; Lee et al, 2003; Bassøe et al, 2003; Rosania et al, 2003, Li et al 2007; Boldyrev et al, 2007; Nadrigny et al, 2007). These dyes have been created using a number of fluorophores, most commonly dipyrromethenboron difluoride (BODIPY), cyanine, carbocyanine, styryl and diaminoxanthene core structures. Typical emission maxima for these organic fluorophores span from 430 to 620 nm. Many of the dyes consequently occupy valuable regions of the visible emission spectrum that preclude use of various fluorescent proteins. As such, the use of these dyes limits the overall levels of multiplexing achievable in HCS assays. Additionally, these dyes often display other suboptimal properties, such as a propensity to photo-bleach, metachromasy and even a tendency to photo-convert to different emission maxima upon brief exposure to broad-band illumination. For example, Lysotracker Red DND-99 (Invitrogen, Carlsbad, Calif., a lysosomal stain) which contains a BODIPY fluorophore in the form of a conjugated multi-pyrrole ring structure upon broad-band illumination, induces molecular changes rendering its photochemical properties similar to those of Lysotracker Green. The similarities between the spectra of Lysotracker Green and converted Lysotracker Red suggest that the third pyrrole ring is taken out of conjugation during the photo-conversion process, leading to a shorter wavelength dye emission. Thus, Lysotracker Red staining for epifluorescence or confocal microscopy, in conjunction with visualization of GFP, leads to spurious results due to photo-conversion of the fluorophore (Freundt et al, 2007).

Acridine orange (Sigma-Aldrich, Saint Louis, Mo. and other sources) has also been used extensively as a fluorescent probe of lysosomes and other acidic subcellular compartments. The metachromasy of acridine organe results, however, in the concomitant emission of green and red fluorescence from stained cells and tissue (Nadrigny et al, 2007). Evanescent-field imaging with spectral fluorescence detection, together with fluorescence lifetime imaging microscopy, demonstrate that green fluorescent acridine orange monomers inevitably coexist with red fluorescing acridine orange dimers in labeled cells. The green monomer emission spectrally overlaps with that of GFP and produces a false apparent co-localization on dual-color images. Due to its complicated photochemistry and interaction with cellular constituents, acridine orange is a particularly problematic label for multi-color fluorescence imaging, both for dual-band and spectral detection. Extreme caution is required, therefore, when deriving quantitative co-localization information from images of GFP-tagged proteins in cells co-labeled with acridine orange.

In principle, the styryl dye, FM4-64 (Invitrogen, Carlsbad, Calif.) is useful for studying endocytosis and vesicular recycling because it is reputed to be confined to the luminal layer of endocytic vesicles. This particular dye distributes throughout intracellular membranes and it indiscriminately stains both the endoplasmic reticulum and nuclear envelope (Zal et al, 2006). Though the different pools of dye all emit at roughly 700 nm, a spectral shift in fluorescence excitation maximum is observed, however, because the dye present in endocytic vesicles and the endoplasmic reticulum absorbs at 510 nm, while the dye associated with the nuclear matrix absorbs at 622 nm. While this can be used advantageously in order to selectively image the nuclear membrane, the dual absorption properties can be problematic in certain multi-parametric imaging experiments. The shift in peak of the absorption spectrum is not confined to FM dyes. A similar phenomenon has also been reported for Rhodamine 6G, where the dye's absorbance maximum is red-shifted from 527 to 546 nm in a concentration dependent manner (Johnson et al, 1978). Rhodamine 6G is commonly employed to label leukocytes, especially in vascular injury models.

Fluorescent analogs of ceramide are commonly employed to visualize Golgi bodies in live cells. The fluorescence emission maximum of certain BODIPY-labeled ceramides, such as $C_5$-DMD-Ceramide (a.k.a. C5-BODIPY-Cer, Invitrogen, Carlsbad, Calif.), has been shown to depend strongly upon the molar density of the probe in the membrane, shifting in emission maximum from green (~515 nm) to red (~620 nm) with increasing concentration (Pagano et al, 1991). Consequently, in live cells, the Golgi bodies display yellow/orange fluorescence emission (a combination of red and green fluorescence emission), whereas predominantly green fluorescence emission is observed in the endoplasmic reticuli, the nuclear envelope and mitochondria. Due to inherent dual emission characteristics when employing these fluorescent ceramide analogs, co-localization studies with GFP are compromised.

Thus, there is a need for the development of new and better dye molecules with improved photo physical properties, cell-permeability and target specificity to various cell regions. These dye candidates should also have the capability of using in multi color cell analysis for imaging or high-throughput screening.

SUMMARY OF THE INVENTION

The present invention provides a novel compound comprising the structure:

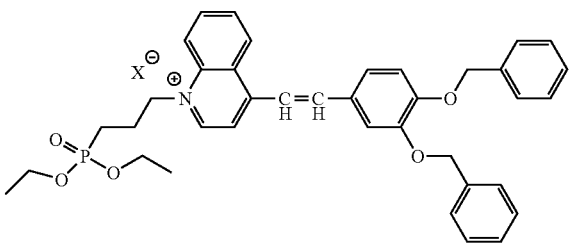 [SMILES: CCOP(=O)(CCC[n+]1ccc(C=Cc2ccc(OCc3ccccc3)c(OCc3ccccc3)c2)c2ccccc21)OCC]

wherein X comprises an anion.

The present invention also provides a novel compound comprising the structure:

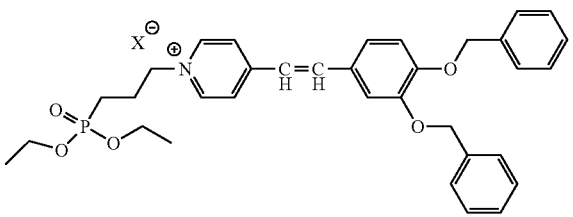 [SMILES: CCOP(=O)(CCC[n+]1ccc(C=Cc2ccc(OCc3ccccc3)c(OCc3ccccc3)c2)cc1)OCC]

wherein X comprises an anion.

This invention further provides a novel compound comprising the structure:

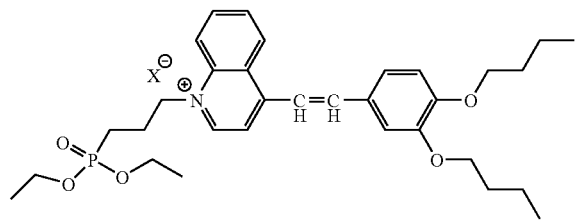 [SMILES: CCCCOc1ccc(C=Cc2cc[n+](CCCP(=O)(OCC)OCC)c3ccccc23)cc1OCCCC]

wherein X comprises an anion.

Also provided by the present invention is a novel compound comprising the structure:

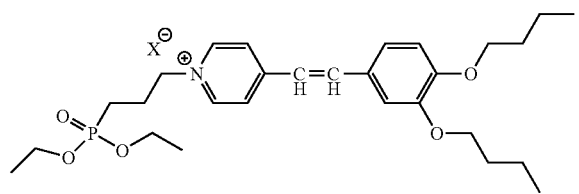 [SMILES: CCCCOc1ccc(C=Cc2cc[n+](CCCP(=O)(OCC)OCC)cc2)cc1OCCCC]

wherein X comprises an anion.

Additionally, this invention provides a novel compound comprising the structure:

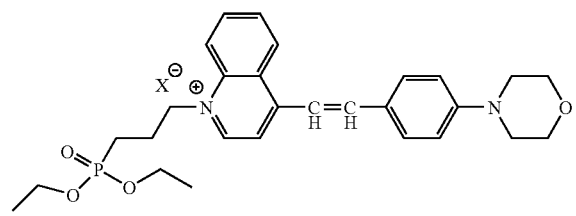 [SMILES: CCOP(=O)(CCC[n+]1ccc(C=Cc2ccc(N3CCOCC3)cc2)c2ccccc21)OCC]

wherein X comprises an anion.

Another novel compound of this invention comprises the structure:

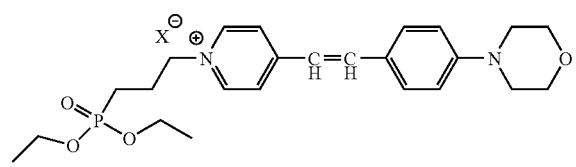 [SMILES: CCOP(=O)(CCC[n+]1ccc(C=Cc2ccc(N3CCOCC3)cc2)cc1)OCC]

wherein X comprises an anion.

Another novel compound provided by the present invention comprises the structure:

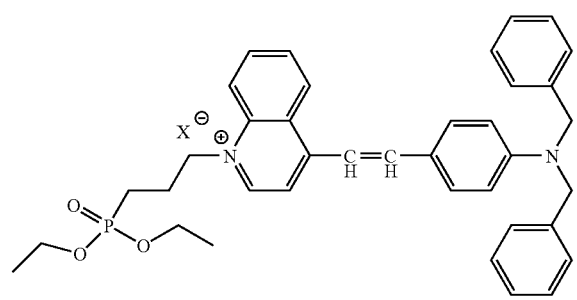 [SMILES: CCOP(=O)(CCC[n+]1ccc(C=Cc2ccc(N(Cc3ccccc3)Cc3ccccc3)cc2)c2ccccc21)OCC]

wherein X comprises an anion.

The present invention further provides a novel compound comprising the structure:

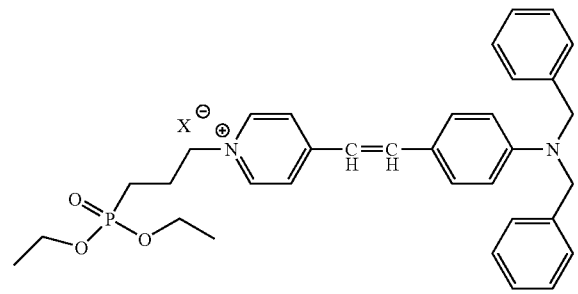 [SMILES: CCOP(=O)(CCC[n+]1ccc(C=Cc2ccc(N(Cc3ccccc3)Cc3ccccc3)cc2)cc1)OCC]

wherein X comprises an anion.

The present invention provides yet another novel compound comprising the structure:

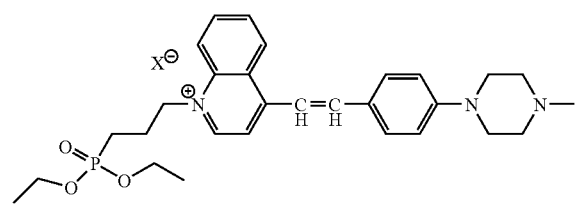 [SMILES: CCOP(=O)(CCC[n+]1ccc(C=Cc2ccc(N3CCN(C)CC3)cc2)c2ccccc21)OCC]

wherein X comprises an anion.

Also provided by the present invention is a novel compound comprising the structure:

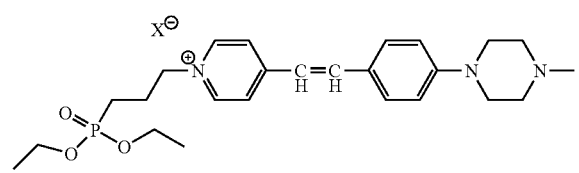 [SMILES: CCOP(=O)(CCC[n+]1ccc(C=Cc2ccc(N3CCN(C)CC3)cc2)cc1)OCC]

wherein X comprises an anion.

Yet another novel compound of this invention comprises the structure:

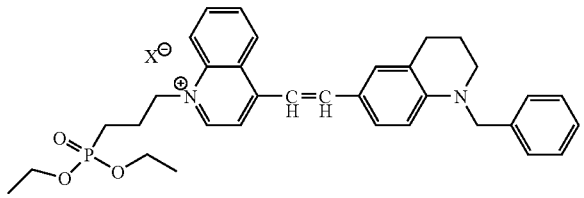 [SMILES: CCOP(=O)(CCC[n+]1ccc(C=Cc2ccc3c(c2)CCCN3Cc2ccccc2)c2ccccc21)OCC]

wherein X comprises an anion.

Still yet another novel compound of this invention comprises the structure:

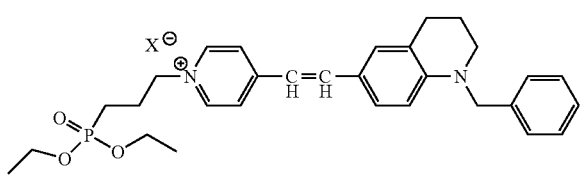 [SMILES: CCOP(=O)(CCC[n+]1ccc(C=Cc2ccc3c(c2)CCCN3Cc2ccccc2)cc1)OCC]

wherein X comprises an anion.

Additionally, the present invention provides a novel compound comprising the structure:

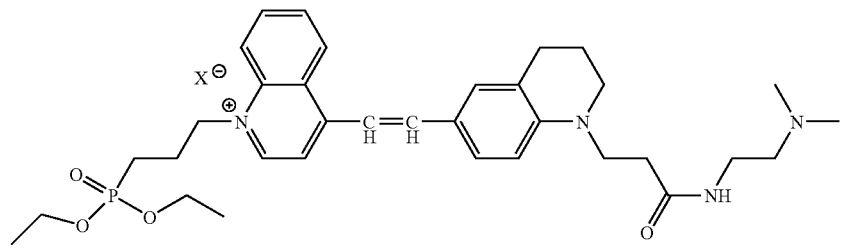 [SMILES: CCOP(=O)(CCC[n+]1ccc(C=Cc2ccc3c(c2)CCCN3CCC(=O)NCCN(C)C)c2ccccc21)OCC]

wherein X comprises an anion.

Further provided by this invention is a novel compound comprising the structure:

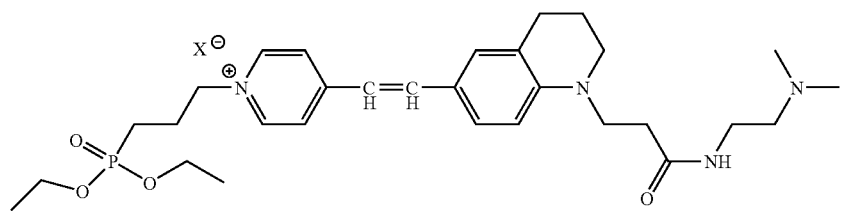 [SMILES: CCOP(=O)(CCC[n+]1ccc(C=Cc2ccc3c(c2)CCCN3CCC(=O)NCCN(C)C)cc1)OCC]

wherein X comprises an anion.

Another novel compound provided by the present invention comprises the structure:

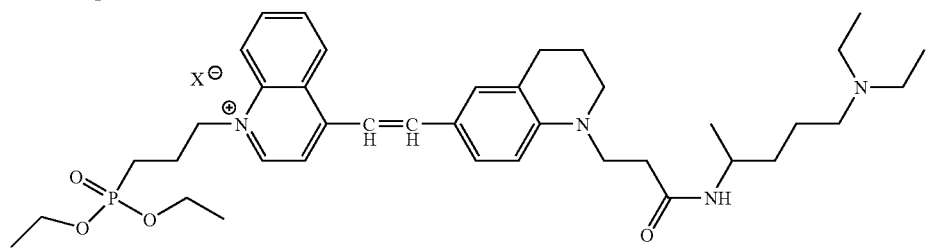 [SMILES: CCOP(=O)(CCC[n+]1ccc(C=Cc2ccc3c(c2)CCCN3CCC(=O)NC(C)CCCN(CC)CC)c2ccccc21)OCC]

wherein X comprises an anion.

Still yet another novel compound of this invention comprises the structure:

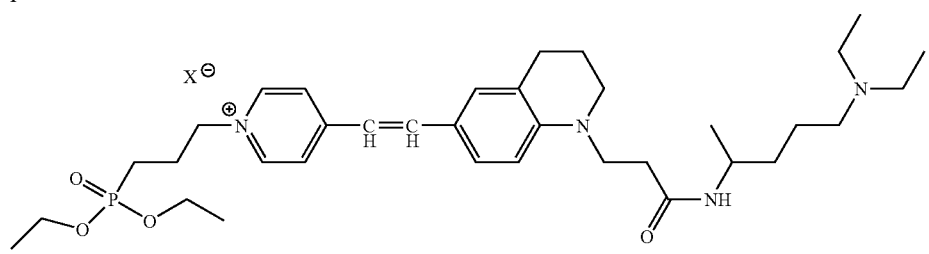

wherein X comprises an anion.

Additionally, the present invention provides a novel compound comprising the structure:

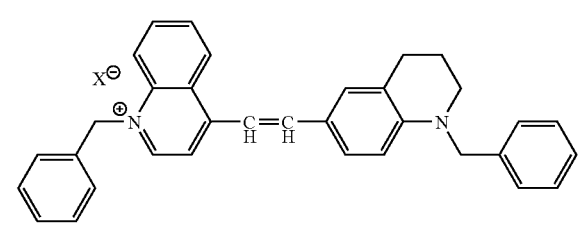 [SMILES: C(=Cc1cc[n+](Cc2ccccc2)c2ccccc12)c1ccc2c(c1)CCCN2Cc1ccccc1]

wherein X comprises an anion.

Still yet another novel compound of this invention comprises the structure:

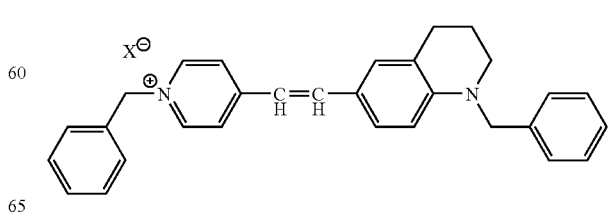

wherein X comprises an anion.

Another novel compound provided by the present invention comprises the structure:

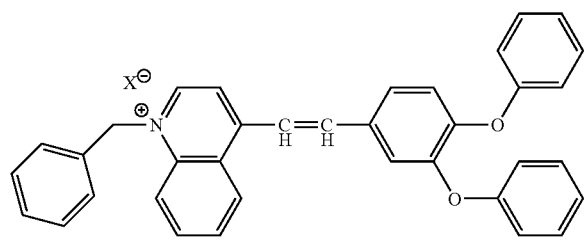 [SMILES: C(=Cc1cc[n+](Cc2ccccc2)c2ccccc12)c1ccc(Oc2ccccc2)c(Oc2ccccc2)c1]

wherein X comprises an anion.

Further provided by this invention is a novel compound comprising the structure:

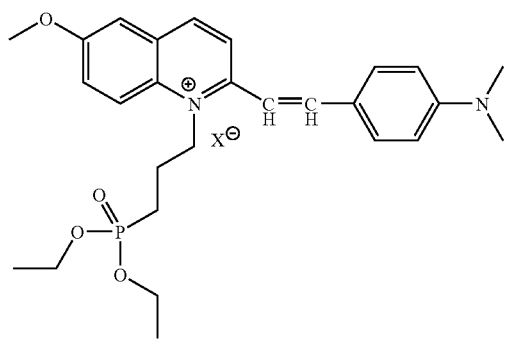

wherein X comprises an anion.

The present invention provides a method for identifying specific organelles or regions in cells of interest comprising the first step (A) of providing (i) the cells of interest; and (ii) any of the compounds of aforementioned claims, followed by incubating (B) the cells of interest (i) with the compound (II); and identifying the organelles or regions in the cells of interest.

Further provided by this invention is a method of labeling target molecules comprising the steps of (a) providing: (i) a sample containing such target molecules; and (ii) any of the novel compounds just described above, wherein the compound or compounds have been modified to comprise at least one reactive group; and (b) attaching any of the compound or compounds (II) by means of the reactive group to the target molecules in the sample (i), thereby labeling the target molecules.

Also provided by this invention is a kit for identifying organelles or regions in cells of interest or in a sample containing cells of interest. The kit contains in packaged combination the following components or elements: (A) any of the aforementioned compounds, (B) optional buffers; and (C) instructions or a protocol for recommended use of the kit.

DESCRIPTION OF THE INVENTION

Figure 1A:
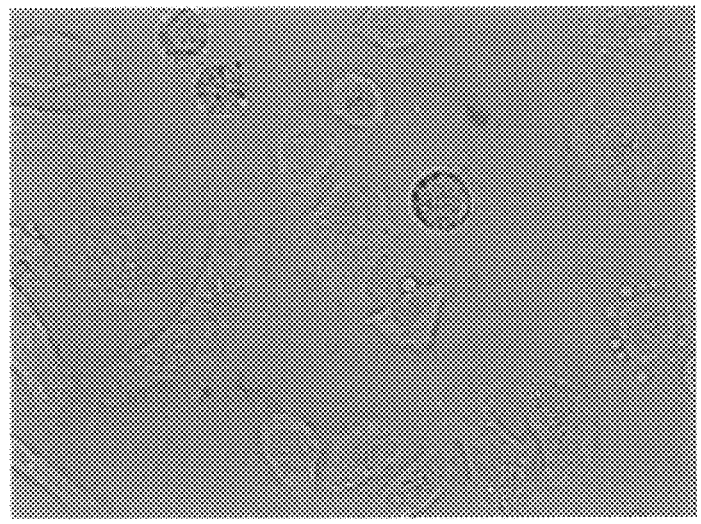
FIG. 1 are micrographs that show staining with Dye 1 the endoplasmic reticulum in HeLa human cervical carcinoma cell line.

The present invention provides fluorescent dyes and labeled reagents that may be used in the detection or quantification of desirable target molecules and for localization to specific organelles or regions in cells of interest. Many if not most of these dyes may be used free in solution where the binding of the dye to the target molecule provides increase fluorescence. Motivation for research in this area is drawn from the acute need for intracellular, tissue, and whole organism imaging. The present invention provides a family of cell-permeable organic probes that spontaneously localize to specific subcellular organelles, cell domains and cell regions which can be readily used in combination with other commonly used UV- and visible excitable organic fluorochromes and fluorescent proteins in multi-color imaging and detection applications. These organic probes can be used in concert with the other fluorochromes to report drug or compound effects in the dynamic context of the living whole cell.

The present dye series is based on cyanine chromophore that is modified by the addition of groups as exemplified by phosphonates and its derivatives. Other dyes have been modified by the addition of lipophilic groups such as long ($\geq 4$) alkyl chains, cationic groups such as alkyl or dialkyl amines and hydrophobic groups such as benzyl. Dyes may also be modified by both charged and polar groups.

It is also understood that when a dye comprises anionic group, there will also be a cationic counterion present. Any cation may serve this purpose as long as it doesn't interfere with the use of the dye. Examples of cations that may serve as counterions can include but not be limited to hydrogen, sodium, potassium, lithium, calcium, cesium, ammonium, alkyl ammonium, alkoxy ammonium and pyridinium. It is also understood that when a dye comprises a cationic group, there will also be an anionic counterion present. Any anion may serve this purpose as long as it doesn't interfere with the use of the dye. Examples of anions that may serve as counterions can include but not be limited to halides such as a bromide, chloride, fluoride and iodide. Other examples can include but not be limited to perchlorate ($ClO_4^-$), sulfate ($SO_4^=$), sulfonate, alkane sulfonate, aryl sulfonate, phosphate, tosylate, mesylate and tetrafluoroborate moieties. In some cases the counterion or counterions are provided by the dye being a salt where they exist as separate ionic species. In other cases, the counterion or counterions may be present as part of the compound (sometimes called inner salts). It is understood that there may also be a combination of ions that are provided by the compound and salts. With regard to acid moieties that are shown in forms such as COOH it is also understood that these compounds may be found in ionized forms such as COO$^-$.

It should also be appreciated by those skilled in the art that the stoichiometric number of counterion or counterions which balance the charge or charges on the compound can be the same or they can be different provided that the counterions balance the charge(s) on the compound. The combination of counterions can be selected from any of the above mentioned anions. This applies for the combination of cations also.

It should be further appreciated by those skilled in the art that the foregoing descriptions of the anions and their stoichiometric number and/or combination are applicable to the compounds and dyes of the present invention, and to methods which use these compounds and dyes.

Alkyl or alkoxy R groups may be substituted or unsubstituted. Examples of substitutions can include but not be limited to one or more fluorine, chlorine, bromine, iodine, hydroxy, carboxy, carbonyl, amino, cyano, nitro or azido groups as well as other alkyl or alkoxy groups. The length of the alkoxy groups may be as desired. For instance, they may independently comprise from 1 to 18 carbons in length. They may be shorter as well, for instance they may be only 1 to 6 carbons in length in a dye molecule of the present invention.

The polar groups, charged groups and other substituents may be connected to the dye directly or they may be connected by a linker arm comprising carbon, nitrogen, sulfur, oxygen or any combination thereof. The linker arm may be saturated or unsaturated, linear or branched, substituted or unsubstituted as well as any combination of the foregoing.

In one aspect of the present invention, novel dyes that are based upon styryl cyanine dyes are disclosed. These dyes can comprise a picoline or quinoline moieties or their derivatives. In one embodiment the dyes have the general structure:

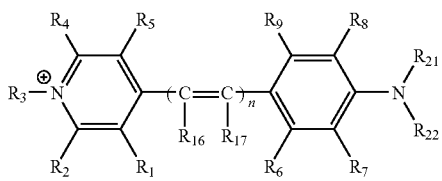

wherein n can be 1, 2 or 3;
wherein at least one of $R_1$, $R_2$, $R_3$, $R_4$, $R_5$, $R_6$, $R_7$, $R_8$, $R_9$, $R_{21}$ or $R_{22}$ comprises Q wherein Q comprises a sulfonate (SO$_3^-$), a sulfonate ester (SO$_2$ER$_{13}$), a sulfoxide (SOR$_{13}$), a sulfone (SO$_2$CR$_{13}$R$_{14}$R$_{15}$), a sulfonamide (SO$_2$NR$_{13}$R$_{14}$), a phosphate (PO$_4^=$), a phosphate monoester (PO$_3^-$ER$_{13}$), a phosphate diester (PO$_2$ER$_{13}$ER$_{14}$), a phosphonate (PO$_3^=$) a phosphonate monoester (PO$_2^-$ER$_{13}$) a phosphonate diester (POER$_{13}$ER$_{14}$), a thiophosphate (PSO$_3^=$), a thiophosphate monoester (PSO$_2^-$ER$_{13}$) a thiophosphate diester (PSOER$_{13}$ER$_{14}$), a thiophosphonate (PSO$_2^=$), a thiophosphonate monoester (PSO$^-$ER$_{13}$) a thiophosphonate diester (PSER$_{13}$ER$_{14}$), a phosphonamide (PONR$_{13}$R$_{14}$NR$_{19}$R$_{20}$), its thioanalogue (PSNR$_{13}$R$_{14}$NR$_{19}$R$_{20}$), a phosphoramide (PONR$_{13}$R$_{14}$NR$_{15}$NR$_{19}$R$_{20}$), its thioanalogue (PSNR$_{13}$R$_{14}$NR$_{15}$NR$_{19}$R$_{20}$), a phosphoramidite (PO$_2$R$_{19}$NR$_{13}$R$_{14}$) or its thioanalogue (POSR$_{19}$NR$_{13}$R$_{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_8$, $R_9$, $R_{21}$ or $R_{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, a benzyl group wherein said benzyl group is substituted or unsubstituted or when taken together, $R_1$ and $R_2$, $R_2$ and $R_3$, $R_3$ and $R_4$, $R_4$ and $R_5$, $R_5$ and $R_{16}$, $R_{16}$ and $R_{17}$, $R_{17}$ and $R_9$, $R_9$ and $R_8$, $R_9$ and $R_{21}$, $R_{21}$ and $R_{22}$, $R_{22}$ and $R_7$, and $R_7$ and $R_6$ may form a 5 or 6 membered ring which may be saturated or unsaturated, substituted or unsubstituted;

wherein Z comprises a carboxyl group (CO$_2^-$), a carbonate ester (COER$_{13}$), a sulfonate (SO$_3^-$), a sulfonate ester (SO$_2$ER$_{13}$), a sulfoxide (SOR$_{13}$), a sulfone (SO$_2$CR$_{13}$R$_{14}$R$_{15}$), a sulfonamide (SO$_2$NR$_{13}$R$_{14}$), a phosphate (PO$_4^=$), a phosphate monoester (PO$_3^-$ER$_{13}$), a phosphate diester (PO$_2$ER$_{13}$ER$_{14}$), a phosphonate (PO$_3^=$) a phosphonate monoester (PO$_2^-$ER$_{13}$) a phosphonate diester (POER$_{13}$ER$_{14}$), a thiophosphate (PSO$_3^=$), a thiophosphate monoester (PSO$_2^-$ER$_{13}$) a thiophosphate diester (PSOER$_{13}$ER$_{14}$), a thiophosphonate (PSO$_2^=$), a thiophosphonate monoester (PSO$^-$ER$_{13}$) a thiophosphonate diester (PSER$_{13}$ER$_{14}$), a phosphonamide (PONR$_{13}$R$_{14}$NR$_{19}$R$_{20}$), its thioanalogue (PSNR$_{13}$R$_{14}$NR$_{19}$R$_{20}$), a phosphoramide (PONR$_{13}$R$_{14}$NR$_{15}$NR$_{19}$R$_{20}$), its thioanalogue (PSNR$_{13}$R$_{14}$NR$_{15}$NR$_{19}$R$_{20}$), a phosphoramidite (PO$_2$R$_{19}$NR$_{13}$R$_{14}$) or its thioanalogue (POSR$_{19}$NR$_{13}$R$_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R_1$, $R_2$, $R_3$, $R_4$, $R_5$, $R_6$, $R_7$, $R_8$, $R_9$, $R_{21}$ or $R_{22}$ may further comprise a heteroatom containing side chain wherein said side chain is joined to the R group by a linkage which comprises an ether linkage (—OR$_{25}$), a thioether linkage (—SR$_{25}$), or an amine linkage (—NR$_{25}$R$_{26}$ or —N$^+$R$_{25}$R$_{26}$R$_{27}$), and wherein R$_{25}$, R$_{26}$ and R$_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, R$_{25}$ and R$_{26}$, and R$_{26}$ and R$_{27}$ independently comprise a five or six membered ring, and wherein any of R$_{25}$, R$_{26}$ or R$_{27}$ may further comprise said heteroatom containing side chain.

When $R_4$ and $R_5$ comprise alkyl chains that are joined together, a quinoline moiety can be formed, the dye thereby having the general structure:

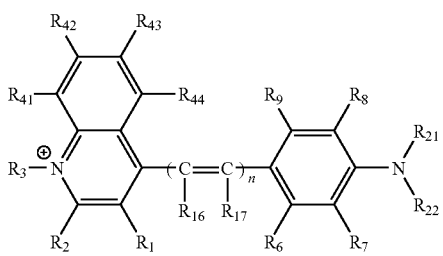

where $R_{41}$, $R_{42}$, $R_{43}$ and $R_{44}$ are as described previously for $R_1$, $R_2$, $R_3$, $R_4$, $R_5$, $R_6$, $R_7$, $R_8$, $R_9$, $R_{21}$ and $R_{22}$.

In another embodiment the dyes have the general structure:

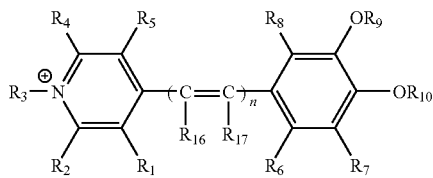

wherein n can be 1, 2 or 3;

wherein at least one of $R_1$, $R_2$, $R_3$, $R_4$, $R_5$, $R_6$, $R_7$, $R_8$, $R_9$ or $R_{10}$ comprises Q wherein Q comprises a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^=$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_9$, $R_9$ or $R_{10}$ or can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, a benzyl group wherein said benzyl group is substituted or unsubstituted or when taken together, $R_1$ and $R_2$, $R_2$ and $R_3$, $R_3$ and $R_4$, $R_4$ and $R_5$, $R_5$ and $R_{16}$, $R_{16}$ and $R_{17}$, $R_{17}$ and $R_8$, $R_9$ and $R_8$, $R_9$ and $R_{10}$, $R_{10}$ and $R_7$, and $R_7$ and $R_6$ may form a 5 or 6 membered ring which may be saturated or unsaturated, substituted or unsubstituted;

wherein Z comprises a carboxyl group ($CO_2^-$), a carbonate ester ($COER_{13}$), a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($POER_{13}ER_{14}$), a phosphonate ($PO_3^=$) a phosphonate monoester ($PO_2ER_{13}$) a phosphonate diester ($POER_{13}ER_{14}$), a thiophosphate ($PSO_3^=$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R_1$, $R_2$, $R_3$, $R_4$, $R_5$, $R_6$, $R_7$, $R_8$, $R_9$ or $R_{10}$ may further comprise a heteroatom containing side chain wherein said side chain is joined to the R group by a linkage which comprises an ether linkage ($-OR_{25}$), a thioether linkage ($-SR_{25}$), or an amine linkage ($-NR_{25}R_{26}$ or $-N^+R_{25}R_{26}R_{27}$), and wherein $R_{25}$, $R_{26}$ and $R_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R_{25}$ and $R_{26}$, and $R_{26}$ and $R_{27}$ independently comprise a five or six membered ring, and wherein any of $R_{25}$, $R_{26}$ or $R_{27}$ may further comprise said heteroatom containing side chain.

When $R_4$ and $R_5$ comprise alkyl chains that are joined together, a quinoline moiety can be formed, the dye thereby having the general structure:

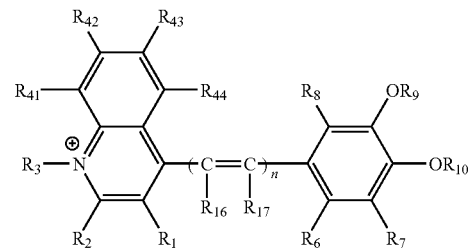

where $R_{41}$, $R_{42}$, $R_{43}$ and $R_{44}$ are as described previously for $R_1$, $R_2$, $R_3$, $R_4$, $R_5$, $R_6$, $R_7$, $R_8$, $R_9$, $R_{21}$ and $R_{22}$.

In yet another embodiment of the present invention, the styryl dye comprises a 2-picoline or quinaldine moiety. As such, these dyes have the structure:

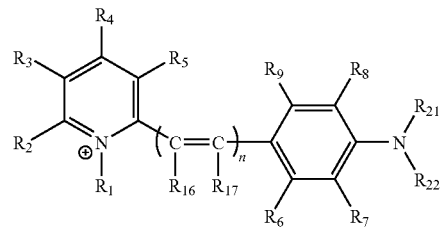

wherein n can be 1, 2 or 3;

wherein at least one of $R_1$, $R_2$, $R_3$, $R_4$, $R_5$, $R_6$, $R_7$, $R_8$, $R_9$, $R_{21}$ or $R_{22}$ comprises Q wherein Q comprises a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^-$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Q is attached directly, or indirectly through a linker arm comprising carbon, sulfur, oxygen, nitrogen, or any combinations thereof and wherein said linker arm may be saturated or unsaturated, linear or branched, substituted or unsubstituted or any combinations thereof and wherein when Q is a sulfonamide, it does not comprise a terminal reactive group or a linker joining the dye to a target molecule;

wherein $R_{13}$, $R_{14}$, $R_{15}$, $R_{19}$ and $R_{20}$ can be hydrogen, a halogen, an amino group, an alkyl group wherein said alkyl group is saturated or unsaturated, linear or branched, substituted or unsubstituted, an alkoxy group wherein said alkoxy group is saturated or unsaturated, branched or linear, substituted or unsubstituted, or when taken together $R_{13}$ and $R_{14}$ form a five or six membered ring;

wherein $R_{16}$, $R_{17}$ and the remaining $R_1$, $R_2$, $R_3$, $R_4$, $R_5$, $R_6$, $R_7$, $R_8$, $R_9$, $R_{21}$ or $R_{22}$ can independently be hydrogen, Z, an alkyl group wherein said alkyl group is saturated or unsaturated, linear or branched, substituted or unsubstituted, an alkoxy group wherein said alkoxy group is saturated or unsaturated, branched or linear, substituted or unsubstituted, a benzyl group wherein said benzyl group is substituted or unsubstituted or when taken together, $R_1$ and $R_2$, $R_2$ and $R_3$, $R_3$ and $R_4$, $R_4$ and $R_5$, $R_5$ and $R_{16}$, $R_{16}$ and $R_{17}$, $R_{17}$ and $R_9$, $R_9$ and $R_8$, $R_9$ and $R_{21}$, $R_{21}$ and $R_{22}$, $R_{22}$ and $R_7$, and $R_7$ and $R_6$ may form a 5 or 6 membered ring;

wherein Z comprises a carboxyl group ($CO_2^-$), a carbonate ester ($COER_{13}$), a sulfonate ($SO_3^-$), a sulfonate ester ($SO_2ER_{13}$), a sulfoxide ($SOR_{13}$), a sulfone ($SO_2CR_{13}R_{14}R_{15}$), a sulfonamide ($SO_2NR_{13}R_{14}$), a phosphate ($PO_4^=$), a phosphate monoester ($PO_3^-ER_{13}$), a phosphate diester ($PO_2ER_{13}ER_{14}$), a phosphonate ($PO_3^=$) a phosphonate monoester ($PO_2^-ER_{13}$) a phosphonate diester ($POER_{13}ER_{14}$), a thiophosphate ($PSO_3^-$), a thiophosphate monoester ($PSO_2^-ER_{13}$) a thiophosphate diester ($PSOER_{13}ER_{14}$), a thiophosphonate ($PSO_2^=$), a thiophosphonate monoester ($PSO^-ER_{13}$) a thiophosphonate diester ($PSER_{13}ER_{14}$), a phosphonamide ($PONR_{13}R_{14}NR_{19}R_{20}$), its thioanalogue ($PSNR_{13}R_{14}NR_{19}R_{20}$), a phosphoramide ($PONR_{13}R_{14}NR_{15}NR_{19}R_{20}$), its thioanalogue ($PSNR_{13}R_{14}NR_{15}NR_{19}R_{20}$), a phosphoramidite ($PO_2R_{19}NR_{13}R_{14}$) or its thioanalogue ($POSR_{19}NR_{13}R_{14}$) where E can be independently O or S;

wherein Z is attached directly, or indirectly through a linker arm comprising carbon, sulfur, oxygen, nitrogen, and any combinations thereof and wherein said linker arm may be saturated or unsaturated, linear or branched, substituted or unsubstituted and any combinations thereof;

and wherein any of $R_1$, $R_2$, $R_3$, $R_4$, $R_5$, $R_6$, $R_7$, $R_8$, $R_9$, $R_{21}$ or $R_{22}$ may further comprise a heteroatom containing side chain wherein said side chain is joined to the R group by a linkage which comprises an ether linkage ($-OR_{25}$), a thioether linkage ($-SR_{25}$), or an amine linkage ($-NR_{25}R_{26}$ or $-N^+R_{25}R_{26}R_{27}$), and wherein $R_{25}$, $R_{26}$ and $R_{27}$ independently comprise hydrogen, Z, an alkyl group wherein said alkyl group is saturated or unsaturated, linear or branched, substituted or unsubstituted, an alkoxy group that is saturated or unsaturated, branched or linear, substituted or unsubstituted, or when taken together, $R_{25}$ and $R_{26}$, and $R_{26}$ and $R_{27}$ independently comprise a five or six membered ring, and wherein any of $R_{25}$, $R_{26}$ or $R_{27}$ may further comprise said heteroatom containing side chain.

When $R_2$ and $R_3$ comprise alkyl chains that are joined together, a quinaldine moiety can be formed, the dye thereby having the general structure:

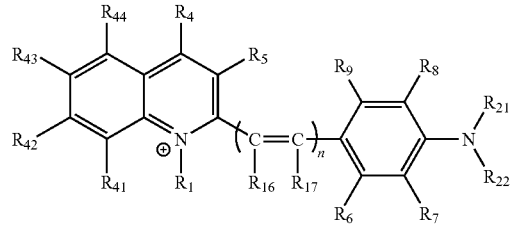

where $R_{41}$, $R_{42}$, $R_{43}$ and $R_{44}$ are as described previously for $R_1$, $R_2$, $R_3$, $R_4$, $R_5$, $R_6$, $R_7$, $R_8$, $R_9$, $R_{21}$ and $R_{22}$.

Complex Ring Structures

As described above some of the R groups may be joined together to form one or more fused 5 or 6 membered ring structures. It is understood that the complex rings that are formed by closure of R groups may be further substituted with any of the R groups described previously. Examples of complex rings that may be formed for the picoline or quinoline portion of cyanine dyes can comprise but not be limited to:

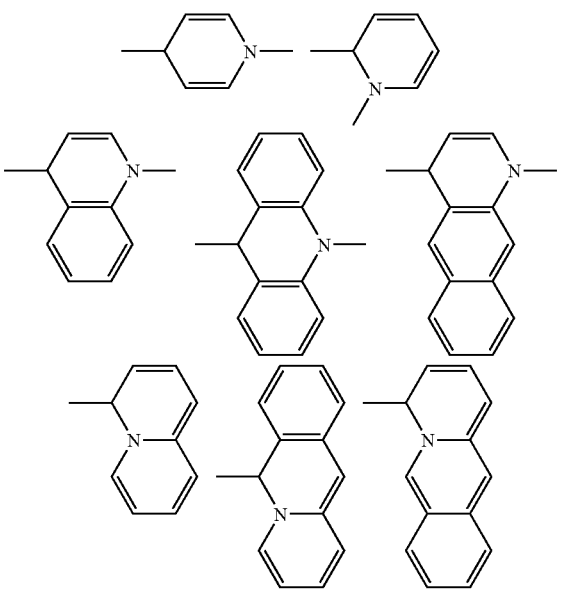

Examples of rings and complex rings that may be part of the asymmetric portion of a styryl dye can comprise but not be limited to:

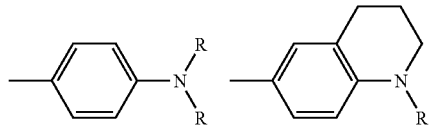

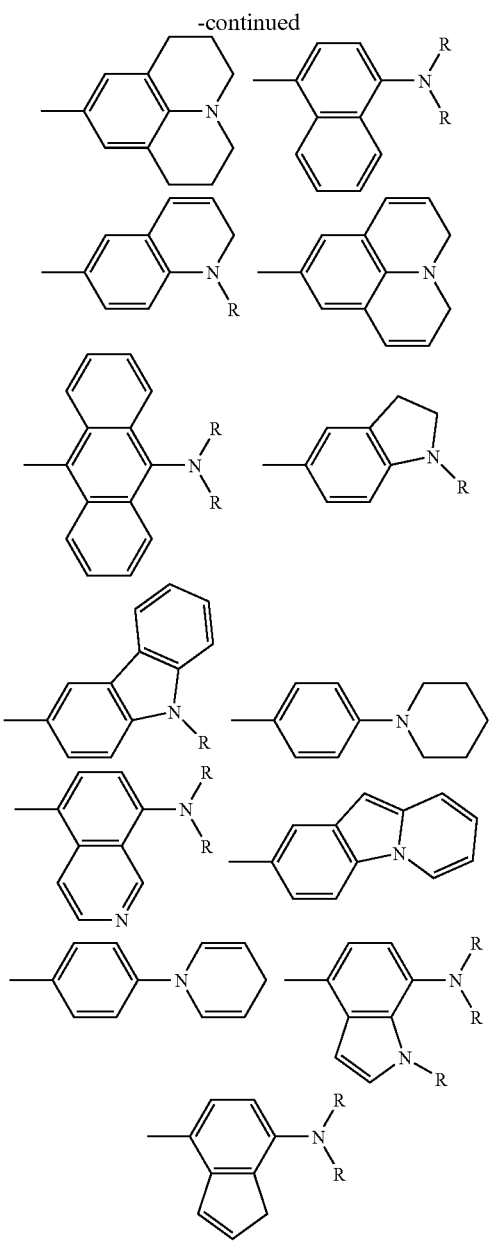

Reactive Groups and Targets

In another aspect of the present invention, one of the R groups is a reactive group thereby allowing the dyes of the present invention to be attached to a useful target molecule. Examples of reactive groups that may find use in the present invention can include but not be limited to a nucleophilic reactive group, an electrophilic reactive group, a terminal alkene, a terminal alkyne, a platinum coordinate group or an alkylating agent.

There are a number of different electrophilic reactive groups that may find use with the present invention; examples can include but not be limited to isocyanate, isothiocyanate, monochlorotriazine, dichlorotriazine, 4,6-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-propionamide, glyoxal and aldehyde groups. Nucleophilic reactive groups can include but not be limited to reactive thiol, amine and hydroxyl groups. For purposes of synthesis of dyes, reactive thiol, amine or hydroxyl groups can be protected during various synthetic steps and the reactive groups generated after removal of the protective group. Use of a terminal alkene or alkyne groups for attachment of markers has been previously described in U.S. Patent Application Serial No. 2003/0225247, hereby incorporated by reference. The use of platinum coordinate groups for attachment of other dyes has been previously disclosed in U.S. Pat. No. 5,580,990 and the use of alkyl groups has been previously described in U.S. Pat. No. 6,593,465 B1, both of which patents are hereby incorporated by reference.

Examples of useful target molecules can include but not be limited to a nucleoside, nucleotide, oligonucleotide, polynucleotide, peptide nucleic acid, protein, peptide, enzyme, antigen, antibody, hormone, hormone receptor, cellular receptor, lymphokine, cytokine, hapten, lectin, avidin, strepavidin, digoxygenin, carbohydrate, oligosaccharide, polysaccharide, lipid, liposomes, glycolipid, viral particle, viral component, bacterial cell, bacterial component, eucaryotic cell, eukaryotic cell component, natural drug, synthetic drug, glass particle, glass surface, natural polymers, synthetic polymers, plastic particle, plastic surface, silicaceous particle, silicaceous surface, organic molecule, dyes and derivatives thereof.

The nucleoside, nucleotide, oligonucleotide, or polynucleotide can comprise one or more ribonucleoside moieties, ribonucleotide moieties, deoxyribonucleoside moieties, deoxyribonucleotide moieties, modified ribonucleosides, modified ribonucleotides, modified deoxyribonucleosides, modified deoxyribonucleotides, ribonucleotide analogues, deoxyribonucleotide analogues and any combination thereof.

As described above, the dyes of the present invention may have dyes as targets thereby creating composite dyes. By joining the dyes of the present invention to another dye, unique properties may be enjoyed that are not present in either dye alone. For instance, if one of the dyes of the present invention is joined to another dye such that it creates an extended conjugation system, the spectral characteristics of the dye may be different than either dye component. Another example of this method is where the conjugation systems do not overlap but the proximity allows an internal energy transfer to take place thereby extending the Stokes shift. For an example of this, see U.S. Pat. No. 5,401,847; U.S. Pat. No. 6,008,373 B1 and U.S. Pat. No. 5,800,996, all three of which patents are hereby incorporated by reference. Other properties may also be enhance by this joining, for example, it has been previously described that the joining together of two ethidium bromide molecules generates a dye that has enhanced binding to nucleic acids (U.S. Patent Application Publication No. 2003/0225247, hereby incorporated by reference). Other composite dyes have been described that simultaneously enjoy both properties, i.e. enhanced binding and energy transfer (U.S. Pat. No. 5,646,264, hereby incorporated by reference). Furthermore, these composites dyes are not limited to binary constructs of only two dyes, but may comprise oligomeric or polymeric dyes. These composite dyes may be comprised of the same dye or different dyes may be joined together depending upon the properties desired.

Utility may also be achieved by attaching a dye of the present invention to a target specific moiety. Thus, binding between the target specific moiety and its corresponding target may be monitored by essentially determining the presence or amount of dye that is bound to the target. Well-known examples of such assays are hybridizations between complementary nucleic acids as well as binding that take place between antibodies and their corresponding antigens. Other binding pairs that may be of interest can include but not be limited to ligand/receptor, hormone/hormone receptor, carbohydrate/lectin and enzyme/substrate. Assays may be carried out where one component is fixed to a solid support and a corresponding partner is in solution. By binding to the component fixed to the support, the partner now becomes attached to the support as well. A well-known example of this method is the microarray assays where labeled analytes become bound to discrete sites on the microarray. Homogeneous probe dependent assays are also well known in the art and may take advantage of the present invention. Examples of such methods are energy transfer between adjacent probes (U.S. Pat. No. 4,868,103), the Taqman exonuclease assay (U.S. Pat. No. 5,538,848 and U.S. Pat. No. 5,210,015), Molecular Beacons (U.S. Pat. No. 5,118,801 and U.S. Pat. No. 5,925,517) and various real time assays (U.S. patent application Ser. No. 10/096,076), all of which are incorporated by reference.

Antibodies labeled with dyes of the present invention may be used in various formats. For example, an antibody with one of the dyes of the present invention may be used in an immunofluorescent plate assay or in situ analysis of the cellular location and quantity of various antigenic targets. Antibodies labeled with dyes may also be used free in solution in cell counting or cell sorting methods that use a flow cytometer or for in-vitro and in-vivo imaging of animal models.

The presence or absence of a signal may then be used to indicate the presence or absence of the target itself. An example of this is a test where it is sufficient to know whether a particular pathogen is present in a clinical specimen. On the other hand, quantitative assays may also be carried out where it is not so much the intention of evaluating if a target is present but rather the particular amount of target that is present. An example of this is the previously cited microarray assay where the particular rise or fall in the amount of particular mRNA species may be of interest.

In another embodiment of the present invention, dyes that have been disclosed above as well as dyes described previous literature may be attached to a carrier with a more general affinity. Dyes may be attached to intercalators that in themselves do not provide signal generation but by virtue of their binding may bring a dye in proximity to a nucleic acid. A further example is attachment of dyes to SDS molecules thereby allowing dyes to be brought into proximity to proteins. Thus this embodiment describes the adaptation of a dye or dyes that lack affinity to a general class of molecules may be adapted by linking them to non-dye molecules or macromolecules that can convey such properties.

Various applications may enjoy the benefits of binding the dyes of the present invention to appropriate targets. As described above, staining of macromolecules in a gel is a methodology that has a long history of use. More recent applications that also may find use are real time detection of amplification (U.S. Pat. No. 5,994,056; U.S. Pat. No. 6,174,670 and U.S. patent application Ser. No. 10/096,076, all of which are hereby incorporated by reference), and binding of nucleic acids to microarrays. In situ assays may also find use where the binding of dyes of the present invention is used to identify the location or quantity of appropriate targets.

Selected embodiments of the compounds of this invention include but are not limited to following:

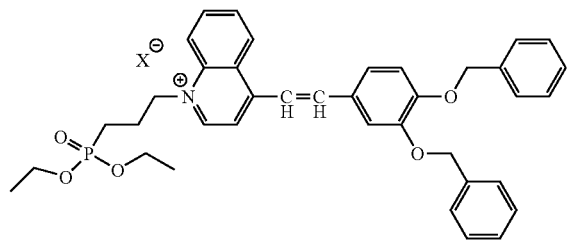 [SMILES: CCOP(=O)(CCC[n+]1ccc(C=Cc2ccc(OCc3ccccc3)c(OCc3ccccc3)c2)c2ccccc21)OCC]

wherein X comprises an anion.

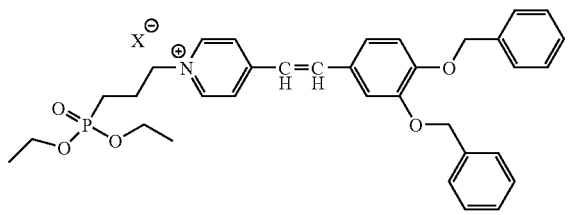 [SMILES: CCOP(=O)(CCC[n+]1ccc(C=Cc2ccc(OCc3ccccc3)c(OCc3ccccc3)c2)cc1)OCC]

wherein X comprises an anion.

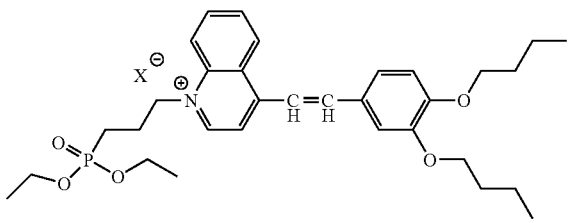 [SMILES: CCCCOc1ccc(C=Cc2cc[n+](CCCP(=O)(OCC)OCC)c3ccccc23)cc1OCCCC]

wherein X comprises an anion.

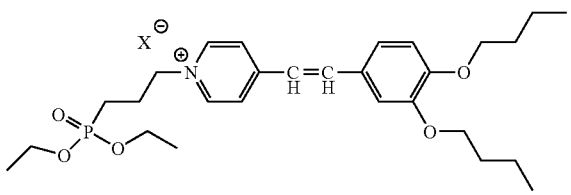

wherein X comprises an anion.

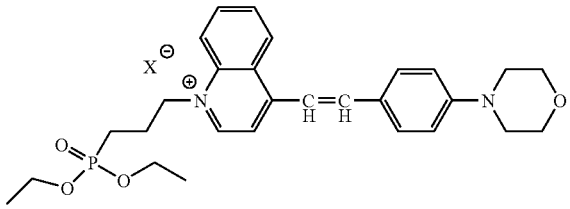 [SMILES: CCOP(=O)(CCC[n+]1ccc(C=Cc2ccc(N3CCOCC3)cc2)c2ccccc21)OCC]

wherein X comprises an anion.

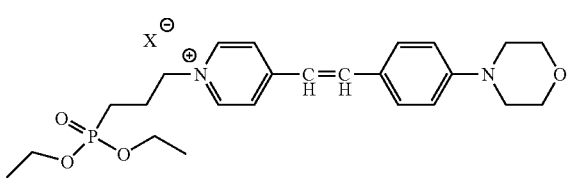 [SMILES: CCOP(=O)(CCC[n+]1ccc(C=Cc2ccc(N3CCOCC3)cc2)cc1)OCC]

wherein X comprises an anion.

21
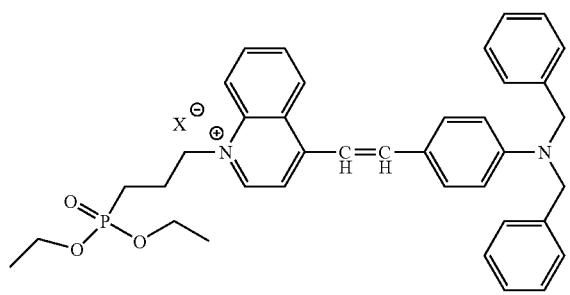 [SMILES: CCOP(=O)(CCC[n+]1ccc(C=Cc2ccc(N(Cc3ccccc3)Cc3ccccc3)cc2)c2ccccc21)OCC]
wherein X comprises an anion.
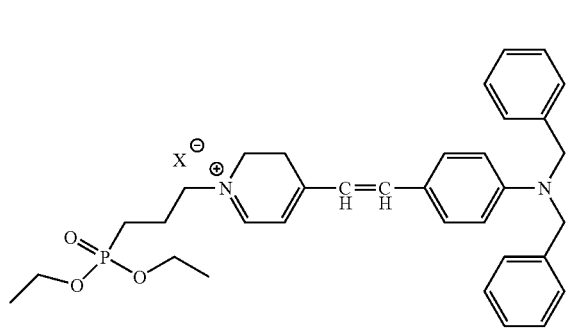 [SMILES: CCOP(=O)(CCC[N+]1=CC=C(C=Cc2ccc(N(Cc3ccccc3)Cc3ccccc3)cc2)CC1)OCC]
wherein X comprises an anion.
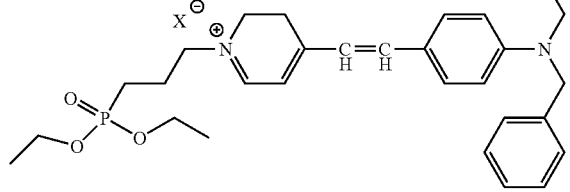
wherein X comprises an anion.
22
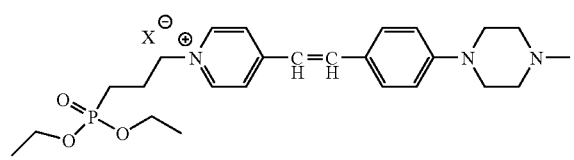 [SMILES: CCOP(=O)(CCC[n+]1ccc(C=Cc2ccc(N3CCN(C)CC3)cc2)cc1)OCC]
wherein X comprises an anion.
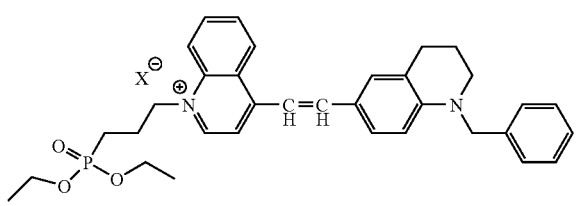 [SMILES: CCOP(=O)(CCC[n+]1ccc(C=Cc2ccc3c(c2)CCCN3Cc2ccccc2)c2ccccc21)OCC]
wherein X comprises an anion.
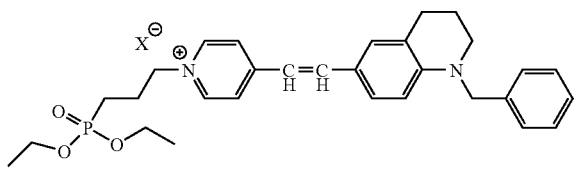 [SMILES: CCOP(=O)(CCC[n+]1ccc(C=Cc2ccc3c(c2)CCCN3Cc2ccccc2)cc1)OCC]
wherein X comprises an anion.
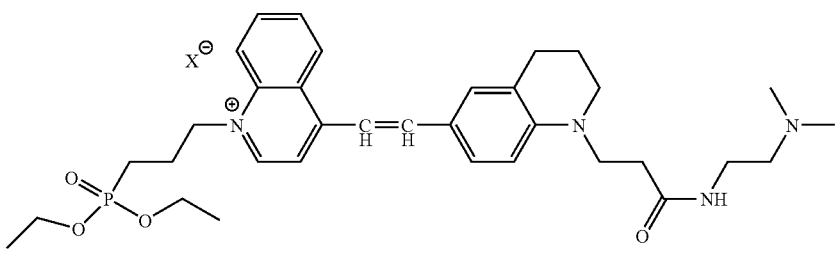 [SMILES: CCOP(=O)(CCC[n+]1ccc(C=Cc2ccc3c(c2)CCCN3CCC(=O)NCCN(C)C)c2ccccc21)OCC]
wherein X comprises an anion.
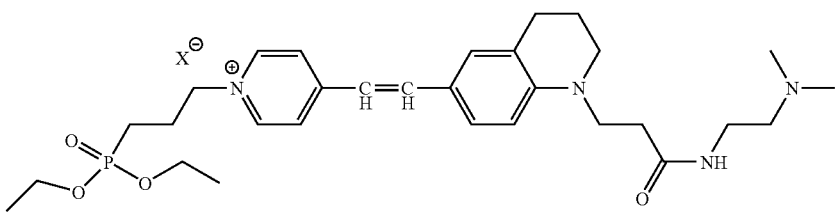 [SMILES: CCOP(=O)(CCC[n+]1ccc(C=Cc2ccc3c(c2)CCCN3CCC(=O)NCCN(C)C)cc1)OCC]
wherein X comprises an anion.

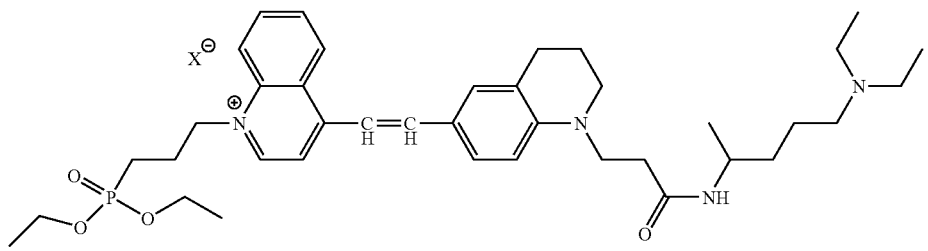 [SMILES: CCOP(=O)(CCC[n+]1ccc(C=Cc2ccc3c(c2)CCCN3CCC(=O)NC(C)CCCN(CC)CC)c2ccccc21)OCC]

wherein X comprises an anion.

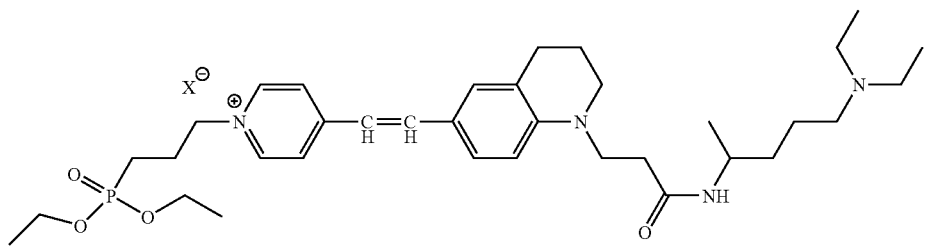 [SMILES: CCOP(=O)(CCC[n+]1ccc(C=Cc2ccc3c(c2)CCCN3CCC(=O)NC(C)CCCN(CC)CC)cc1)OCC]

wherein X comprises an anion.

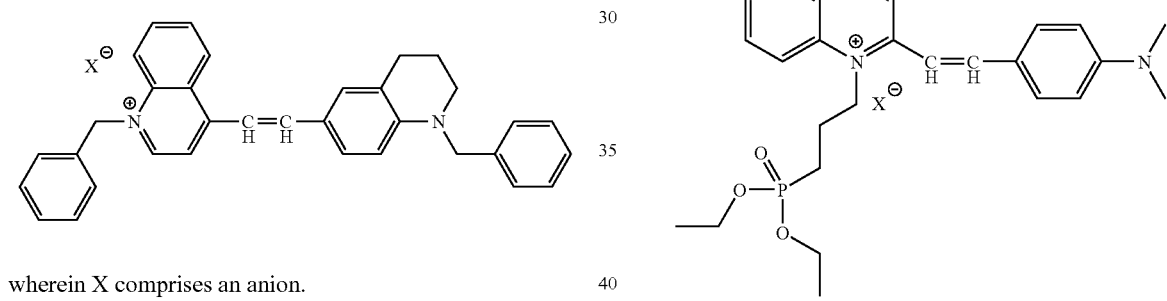

wherein X comprises an anion.

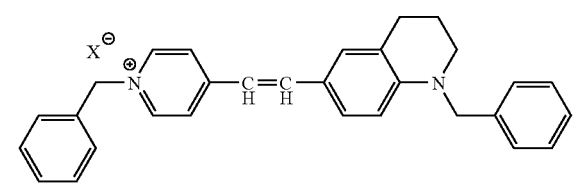 [SMILES: C(=Cc1ccc2c(c1)CCCN2Cc1ccccc1)c1cc[n+](Cc2ccccc2)cc1]

wherein X comprises an anion.

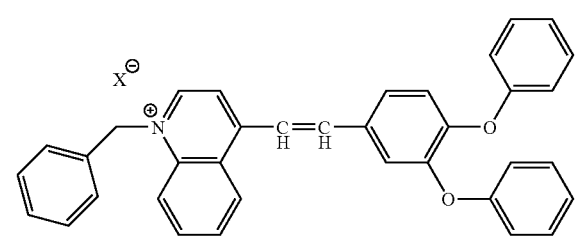 [SMILES: C(=Cc1cc[n+](Cc2ccccc2)c2ccccc12)c1ccc(Oc2ccccc2)c(Oc2ccccc2)c1]

wherein X comprises an anion.

wherein X comprises an anion.

As described above, the anions serve as counterions for the compounds and dyes of the present invention. Examples of cations that may serve as counterions include but are not be limited to hydrogen, sodium, potassium, lithium, calcium, cesium, ammonium, alkyl ammonium, alkoxy ammonium and pyridinium. When a dye comprises a cationic group, an anionic counterion will also be present. Any anion may serve this purpose as long as it doesn't interfere with the use of the dye. Examples of anions that may serve as counterions include but are not limited to halides such as a bromide, chloride, fluoride and iodide. Other examples of anions that can serve as counterions include but are not limited to perchlorate ($ClO_4^-$), sulfate ($SO_4^=$), sulfonate, alkane sulfonate, aryl sulfonate, phosphate, tosylate, mesylate and tetrafluoroborate moieties.

As also described above, in some cases the counterion or counterions are provided by the dye being presented as a salt where it exists as separate ionic species. In other cases, the counterion or counterions may be present as part of the compound (sometimes called inner salts). It is understood that a combination of ions may be provided by the compound and salts. With regard to acid moieties that are shown in forms such as COOH, it should be understood and appreciated that these compounds may be found in ionized forms such as COO⁻. It should also be appreciated by those skilled in the art that the stoichiometric number of counterion or counterions which balance the charge or charges on the compounds of the present invention can be the same or they can be different, provided that the counterions balance the charge(s) on the compound. The combination of counterions can be selected from any of the anions described above. Similarly, the combination of counterions can also be selected from any of the cations described above.

The examples which follow are set forth to illustrate various aspects of the present invention but are not intended in any way to limit its scope as more particularly set forth and defined in the claims that follow thereafter.

DESCRIPTION OF THE PREFERRED EMBODIMENTS

Example 1

Synthesis of Dye 1

(a) Preparation of Ethyl 3-(4-methylquinolinium-1-yl) propylphosphonate (Compound 1)

A mixture of lepidine (1.0 g, 7.0 mmol) and diethyl-(3-bromopropyl)-phosphonate (2.0 g, 7.7 mmol) was heated in a pressure tube at 130° C. for 4 hours. The mixture was allowed to cool to room temperature, and the resulting mass was dissolved in DMF (4 ml). The combined mixture was then added dropwise to ethyl acetate (40 ml). An oily residue was obtained which was washed with ethyl acetate (2×40 ml) and dried under vacuum to yield 1.9 g of Compound 1 which was then used without any further purification. The structure of Compound 1 is given below:

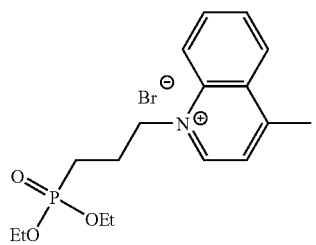

Compound 1

(b) Preparation of Dye 1

A mixture of Compound 1 (0.274 g, 0.68 mmol), 3,4-bis(benzyloxy)benzaldehyde (0.26 g, 0.82 mmol) and piperidine (33 µL, 0.33 mmol) was refluxed in ethanol (5 ml) using a microwave reactor (CEM, 200 W, open vessel) for 20 mins. The reaction mixture was cooled to room temperature and reaction mixture added to diethyl ether (40 mL). Precipitated sticky solid was collected by centrifugation, washed with ether and dried under vacuum. Crude dye was purified on Biotage (Si, 25+M) using a gradient of methanol (2% to 20% over 10 column volume) in chloroform to provide Dye 1 as a yellow residue (57.3 mg). Abs (max, methanol)=443 nm, Em=548 nm. The structure of Dye 1 is given below:

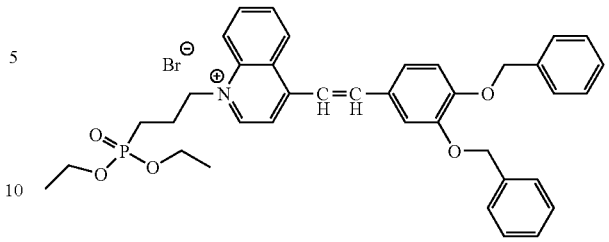

Dye 1

Example 2

Synthesis of Dye 2

(a) Preparation of 3,4-dibutoxybenzaldehyde (Compound 2)

To a solution of 3,4-dihydroxybenzaldehyde (0.5 g, 3.62 mmol) and iodobutane (1.46 g, 7.96 mmol) in ethanol (5 mL), potassium carbonate (1.5 g, 10.9 mmol) was added. Combined mixture was refluxed in the microwave reactor (CEM, 200 W, open vessel) for 1 hour. The reaction mixture was cooled to room temperature, diluted with water (20 mL) and extracted with methylene chloride (2×50 mL). The combined organic layers were washed with water (2×), brine (2×), dried (MgSO₄) and evaporated to provide the product as an oily residue (280 mg). This product was used without any further purification. The structure of Compound 2 is given below:

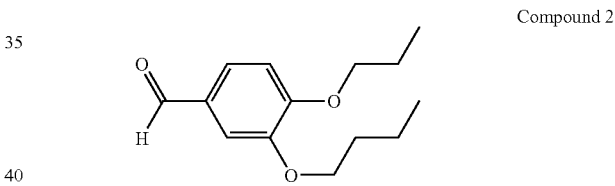

Compound 2

(b) Preparation of Dye 2

A mixture of Compound 1 (0.2 g, 0.5 mmol), Compound 2 (0.14 g, 0.55 mmol) and piperidine (22 µL, 0.22 mmol) was refluxed in ethanol (4 mL) using a microwave reactor (CEM, 200 W, open vessel) for 1 hour. The reaction mixture was cooled to room temperature and solvents were removed in the rotary evaporator. The residue thus obtained was purified on Biotage (Si, SNAP 25 g) using a gradient of methanol (2% to 20% over 10 column volume) in methylene chloride to provide Dye 2 as a yellow residue (47 mg). Abs (max, methanol)=449 nm, Abs (max, PBS)=426 nm. The structure of Dye 2 is given below:

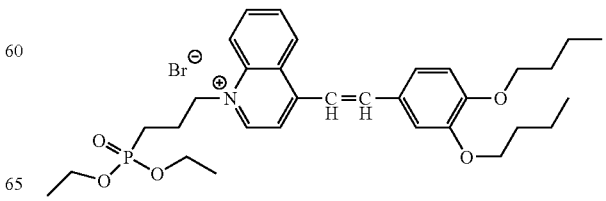

Dye 2

Example 3

Synthesis of Dye 3

(a) Preparation of 1-(3-(diethoxyphosphoryl)propyl)-4-methylpyridinium bromide (Compound 3)

A mixture of picoline (0.5 g, 5.4 mmol) and diethyl(3-bromopropyl)-phosphonate (1.54 g, 5.9 mmol) was heated in a pressure tube at 130° C. for 4 hours. The mixture was allowed to cool to room temperature, and the resulting mass was dissolved in DMF (4 ml). The combined mixture was then added drop wise to ethyl acetate (40 ml). An oily residue was obtained which was washed with ethyl acetate (2×40 ml) and dried under vacuum to yield 1.7 g of Compound 3 which was then used without any further purification. The structure of Compound 3 is given below:

Compound 3

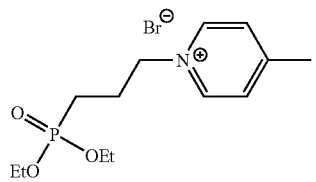

(b) Preparation of Dye 3

A mixture of Compound 2 (77 mg, 0.31 mmol), Compound 3 (100 mg, 0.28 mmol) and piperidine (12 μL, 0.13 mmol) was refluxed in ethanol (2 mL) using a microwave reactor (CEM, 200 W, open vessel) for 1 hour. The reaction mixture was cooled to room temperature and solvents were removed in the rotary evaporator. The residue thus obtained was purified on Biotage (Si, 12+M) using a gradient of methanol (2% to 20% over 10 column volume) in methylene chloride to provide Dye 3 as a yellow residue (57 mg). Abs (max, methanol)=406 nm. The structure of Dye 3 is given below:

Dye 3

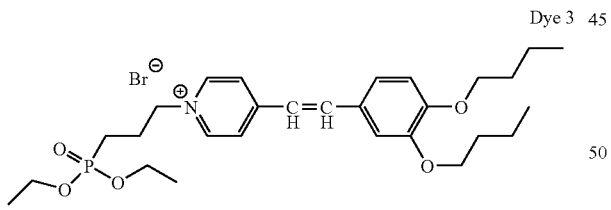

Example 4

Synthesis of Dye 4

The procedure was carried out as described previously in step (b) of Example 1 with Compound 1 (0.27 g, 0.68 mmol), piperidine (33 μL, 0.33 mmol), 4-(4-Formylphenyl)morpholine (0.16 g, 0.82 mmol) and ethanol (5 mL). Purification was carried out on Biotage (SNAP, 50 g) using a gradient of methanol in chloroform (5% to 40% over 10 CV) to provide Dye 4 as an orange residue (74.7 mg). Abs (max, methanol)=500 nm. The structure of Dye 4 is given below:

Dye 4

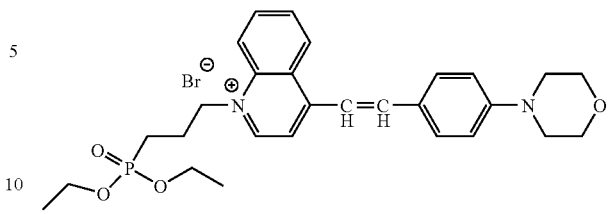

Example 5

Synthesis of Dye 5

(a) Preparation of 4-(dibenzylamino)benzaldehyde (Compound 4)

To an ice cooled DMF (4.2 mL), phosphorous oxychloride (3.5 mL, 36.6 mmol) was added dropwise. The combined mixture was stirred in the ice bath for 30 min followed by dropwise addition of a solution of N,N-dibenzylaniline (5.0 g, 18.3 mmol) in DMF (25 mL) over a period of 20 min. After the addition was complete, the ice bath was removed and reaction mixture stirred at room temperature for 20 hours. An aqueous solution of sodium acetate (25% w/w, 25 mL) was then added to the reaction mixture and it was heated in an oil bath (T=110° C.) for 15 min. The reaction mixture was cooled and poured into ca. 100 ml water and extracted with ethyl acetate. The organic layer was washed twice with water followed by brine, dried over sodium sulfate and then evaporated to dryness to yield 4.33 g of an orange solid (Compound 4) with the Compound 4

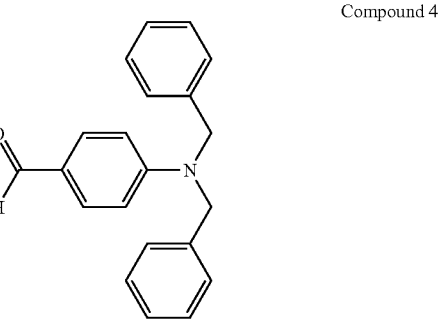

(b) Preparation of Dye 5

The procedure was carried out as described previously in step (b) of Example 1 with Compound 1 (0.27 g, 0.68 mmol), piperidine (33 μL, 0.33 mmol), Compound 4 (0.25 g, 0.82 mmol) and ethanol (5 mL). Purification was carried out on Biotage (Flash, 25+M) using a gradient of methanol in chloroform (3% to 30% over 10 CV) to provide Dye 5 as a purple residue (121.7 mg). Abs (max, methanol)=550 nm. The structure of Dye 5 is given below:

Dye 5

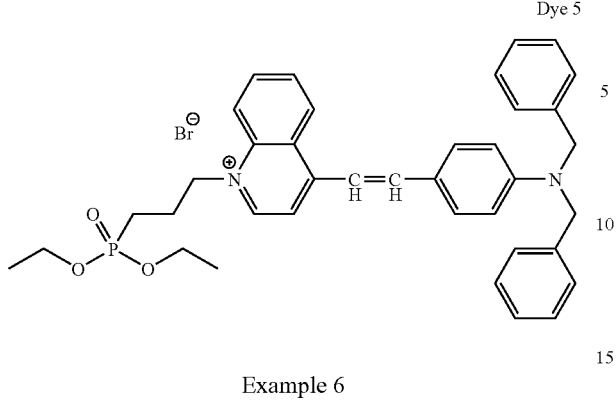

Example 6

Synthesis of Dye 6

The procedure was carried out as described previously in step (b) of Example 1 with Compound 1 (0.27 g, 0.68 mmol), piperidine (33 µL, 0.33 mmol), 4-(4-Methylpiperazinyl)benzaldehyde (0.17 g, 0.82 mmol) and ethanol (5 mL). Purification was carried out by precipitation in ether of a solution of dye in methanol. Dye 6 was obtained as a red solid (300 mg). Abs (max, methanol)=506 nm. The structure of Dye 6 is given below:

Dye 6

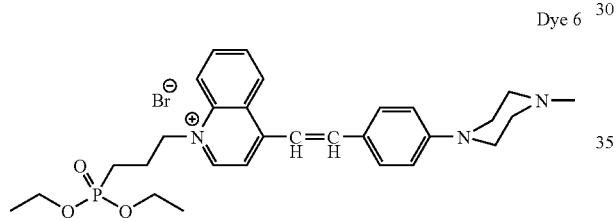

Example 7

Synthesis of Dye 7

(a) Preparation of 1-benzyl-1,2,3,4-tetrahydroquinoline (Compound 5)

A mixture of 1,2,3,4-tetrahydroquinoline (0.5 g, 3.75 mmol), benzyl bromide (0.67 mL, 5.63 mmol) and diisopropylethyl amine (0.98 mL, 5.63 mmol) in DMF (5 mL) was heated in an oil bath (T~120° C.) for 16 hours. Reaction mixture was cooled, added to brine (75 mL) and extracted with ethyl acetate (100 mL). Organic layer was washed with brine (4×) and decolorized with activated charcoal. Upon filtering, it was dried with MgSO$_4$, filtered again and evaporated to dryness to provide Compound 5 as an oily residue (420 mg) with the structure given below:

Compound 5

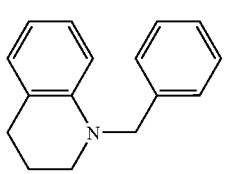

(b) Preparation of 1-benzyl-1,2,3,4-tetrahydroquinoline-6-carbaldehyde (Compound 6)

The procedure was carried out as described previously in step (a) of Example 5 with Compound 5 (0.42 g, 1.88 mmol), POCl$_3$ (355 µL, 3.76 mmol), and DMF (3.5 mL). Compound 6 was obtained (0.36 g) as a viscous liquid and used without any further purification. The structure of Compound 6 is given below:

Compound 6

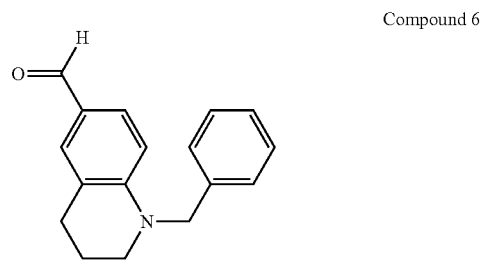 [SMILES: O=Cc1ccc2c(c1)CCCN2Cc1ccccc1]

(c) Preparation of Dye 7

The procedure was carried out as described previously in step (b) of Example 1 with Compound 1 (0.2 g, 0.5 mmol), piperidine (24 µL, 0.24 mmol), Compound 6 (0.15 g, 0.6 mmol) and ethanol (4 mL). Purification was carried out on Biotage (SNAP, 50 g) using a gradient of methanol in chloroform (3% to 30% over 10 CV) to provide Dye 7 as a purple residue (56.1 mg). Abs (max, methanol)=570 nm. The structure of Dye 7 is given below:

Dye 7

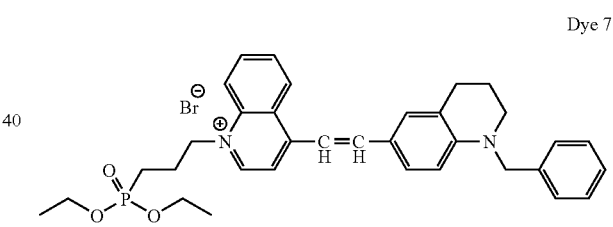

Example 8

Synthesis of Dye 8

(a) Preparation of 3-(3,4-dihydroquinolin-1(2H)-yl) propanoic acid (Compound 7)

A mixture of 1,2,3,4-tetrahydroquinoline (3.0 g, 22.5 mmol) and methyl acrylate (3.9 g, 45.0 mmol) in acetic acid (15 mL) was refluxed for 16 hours. Upon cooling, volatiles were removed in the rotary evaporator and the residue obtained was co-evaporated with methanol (3×20 mL) and then dissolved in methanol (15 mL). To this mixture an aqueous solution of LiOH (1.9 g, 45 mmol) was added and it was stirred at room temperature for 2 hours. Reaction mixture was acidified with conc. HCl to pH~3 and extracted with ethyl acetate. The organic layer was washed twice with water and brine, dried over MgSO$_4$ and evaporated to dryness to yield 2.91 g of Compound 7 as a dark brown viscous liquid. This product was used without any further purification. The structure of Compound 7 is given below:

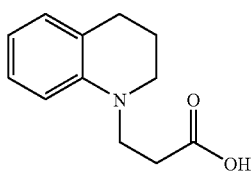

Compound 7

(b) Preparation of 3-(3,4-dihydroquinolin-1(2H)-yl)-N-(2-(dimethylamino)ethyl) propanamide (Compound 8)

To a solution of Compound 7 (1.0 g, 4.9 mmol) in DMF (20 mL), 2-succinimido-1,1,3,3-tetramethyluronium tetrafluoroborate (1.8 g, 5.8 mmol) and N,N-diisopropyl ethylamine (1.8 mL, 10.2 mmol) were added. Combined mixture was stirred at room temperature for 30 mins and then a solution of N,N-dimethylethylenediamine (0.64 g, 7.3 mmol) in DMF (2 mL) was added. After stirring the mixture for additional 1 hour, it was poured in brine (100 mL) and extracted with ethyl acetate (2×75 mL). The combined organic layers were washed with brine (3×100 mL) and dried over MgSO$_4$. The solvent was removed under reduced pressure to provide Compound 8 as brown viscous liquid (0.74 g, 55%). This product was used without further purification. The structure of Compound 8 is given below:

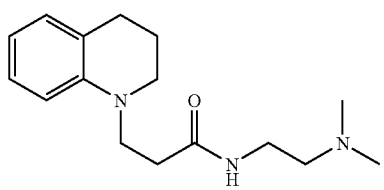

Compound 8

(c) Preparation of N-(2-(dimethylamino)ethyl)-3-(6-formyl-3,4-dihydroquinolin-1(2H)-yl)propanamide (Compound 9)

The procedure was carried out as described previously in step (a) of Example 5 with Compound 8 (0.74 g, 2.7 mmol), POCl$_3$ (506 µL, 5.4 mmol), and DMF (8.6 mL). Compound 9 was obtained (0.31 g) as a viscous yellow liquid and used without any further purification. The structure of Compound 9 is given below:

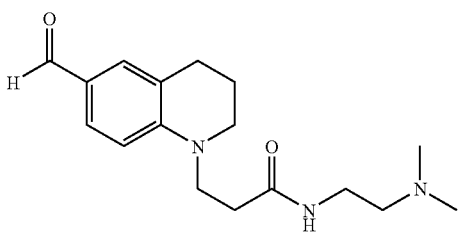

Compound 9

(d) Preparation of Dye 8

The procedure was carried out as described previously in step (b) of Example 1 with Compound 1 (0.2 g, 0.5 mmol), piperidine (25 µL, 0.26 mmol), Compound 9 (0.2 g, 0.65 mmol) and ethanol (4 mL). Purification was carried out on Biotage (SNAP, 25 g) using a gradient of methanol in dichloromethane (2% to 20% over 10 CV) to provide Dye 8 as a purple residue (41.1 mg). Abs (max, methanol)=575 nm. The structure of Dye 8 is given below:

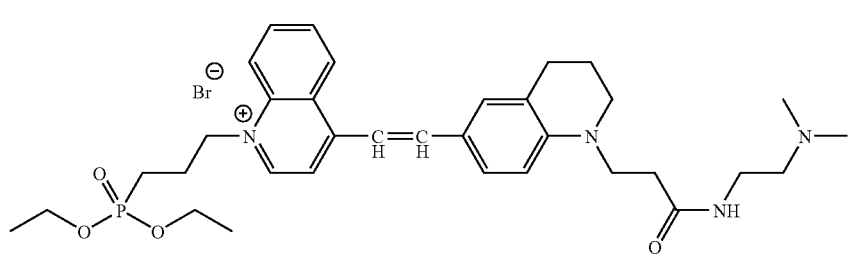

Dye 8

Example 9

Synthesis of Dye 9

(a) Preparation of N-(5-(diethylamino)pentan-2-yl)-3-(3,4-dihydroquinolin-1(2H)-yl)propanamide (Compound 10)

The procedure was carried out as described previously in step (b) of Example 8 with Compound 7 (1.9 g, 9.3 mmol), 2-succinimido-1,1,3,3-tetramethyluronium tetrafluoroborate (3.4 g, 11.2 mmol), N,N-diisopropyl ethylamine (3.4 mL, 19.5 mmol), 2-amino-5-diethylaminopentane (2.2 g, 13.9 mmol) and DMF (40 mL). Compound 10 was obtained (2.64 g) as a viscous liquid and used without any further purification. The structure of Compound 10 is given below:

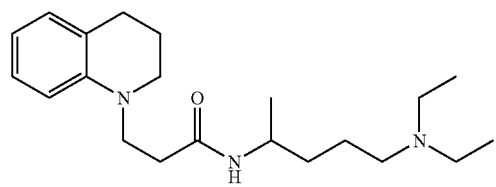

Compound 10

(b) Preparation of N-(5-(diethylamino)pentan-2-yl)-3-(6-formyl-3,4-dihydroquinolin-1(2H)-yl)propanamide (Compound 11)

The procedure was carried out as described previously in step (a) of Example 5 with Compound 10 (2.64 g, 7.6 mmol), POCl₃ (1.5 mL, 15.3 mmol), and DMF (27 mL). Compound 11 was obtained (1.44 g, 51%) as a viscous brown liquid and used without any further purification. The structure of Compound 11 is given below:

Compound 11

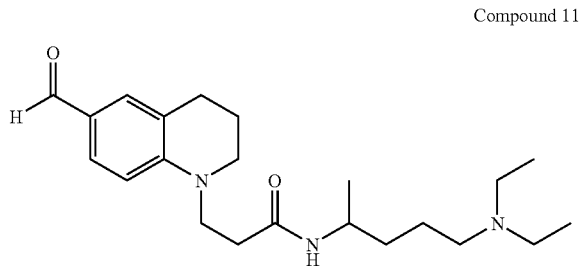 [SMILES: CCN(CC)CCCC(C)NC(=O)CCN1CCCc2cc(C=O)ccc21]

(c) Preparation of Dye 9

This procedure was carried out as described previously in step (b) of Example 1 with Compound 1 (0.1 g, 0.25 mmol), piperidine (13 μL, 0.13 mmol), Compound 11 (0.12 g, 0.33 mmol) and ethanol (2 mL). Purification was carried out on Biotage (SNAP, 25 g) using a gradient of methanol in dichloromethane (2% to 20% over 10 CV) to provide Dye 9 as a purple residue (41.1 mg). Abs (max, methanol)=576 nm. The structure of Dye 9 is given below:

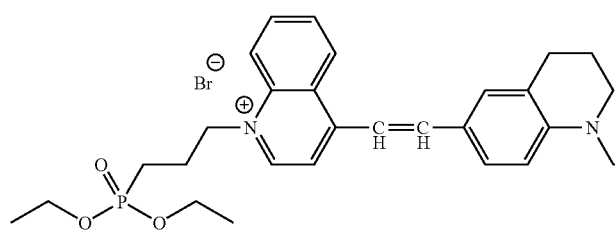

Example 10

Synthesis of Dye 10

(a) Preparation of 1-benzyl-4-methylquinolinium bromide (Compound 12)

To a solution of lepidine (14.3 g, 0.1 mol) in toluene (200 mL), benzyl bromide (34.2 g, 0.2 mol) was added dropwise at room temperature. After the addition, the mixture was heated to reflux for 5 hrs. The mixture was cooled to room temperature; the precipitate formed was collected by filtration, washed with toluene and dried under vacuum to give Compound 12 as yellow solid (18.2 g, 58%). It was used without any further purification. The structure of Compound 12 is given below:

Compound 12

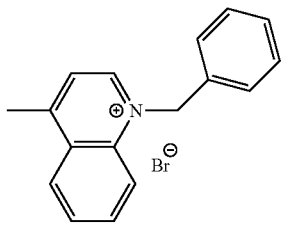

(b) Preparation of Dye 10

The procedure was carried out as described previously in step (b) of Example 1 with Compound 12 (0.1 g, 0.32 mmol), piperidine (15 μL, 0.15 mmol), Compound 6 (0.1 g, 0.38 mmol) and ethanol (2 mL). Purification was carried out on Biotage (SNAP, 25 g) using a gradient of methanol in dichloromethane (1% to 14% over 10 CV) to provide Dye 10 as a purple residue (52.8 mg). Abs (max, methanol)=585 nm. The structure of Dye 10 is given below:

Dye 10

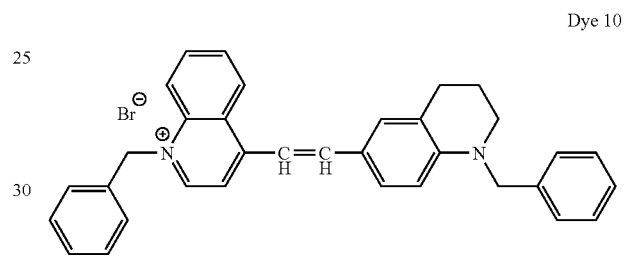

Example 11

Synthesis of Dye 11

The procedure was carried out as described previously in step (b) of Example 1 with Compound 12 (0.25 g, 0.80 mmol), piperidine (38 pt, 0.39 mmol), 3,4-bis(benzyloxy)benzaldehyde (0.3 g, 0.96 mmol) and ethanol (5 mL). Purification was carried out on Biotage (SNAP, 25 g) using a gradient of methanol in dichloromethane (1% to 14% over 10 CV) to provide Dye 11 as a purple residue (95 mg). Abs (max, methanol)=450 nm. The structure of Dye 11 is given below:

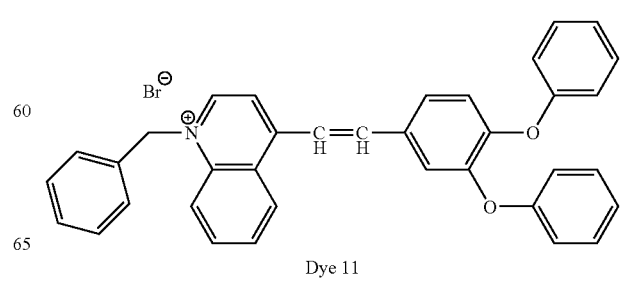

Dye 11

Example 12

Synthesis of Dye 12

(a) Preparation of 1-(3-(diethoxyphosphoryl)propyl)-6-methoxy-2-methylquinolinium bromide (Compound 13)

A mixture of 6-methoxy-2-methylquinoline (1.0 g, 5.8 mmol) and diethyl-(3-bromopropyl)-phosphonate (1.6 g, 6.4 mmol) was heated in a pressure tube at 140° C. for 16 hours. The mixture was allowed to cool to room temperature, and the resulting mass was dissolved in DMF (4 mL). The combined mixture was then added dropwise to ethyl acetate (40 mL). Precipitated purple solid was collected by centrifugation, washed with ethyl acetate (3×40 mL) and dried under vacuum to yield 1.7 g of Compound 13 which was then used without any further purification. The structure of Compound 13 is given below:

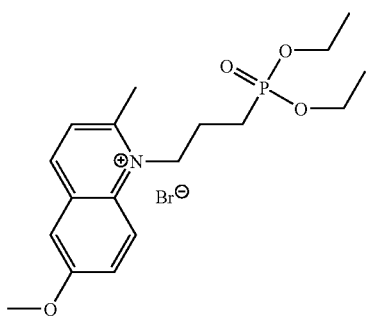

Compound 13

(b) Preparation of Dye 12

The procedure was carried out as described previously in step (b) of Example 1 with Compound 13 (0.2 g, 0.46 mmol), piperidine (22 µL, 0.22 mmol), 4-dimethylamino benzaldehyde (0.08 g, 0.55 mmol) and ethanol (4 mL). Purification was carried out on Biotage (SNAP, 50 g) using a gradient of methanol in dichloromethane (2% to 20% over 10 CV) to provide Dye 12 as a red solid (68 mg). Abs (max, methanol)=518 nm; Abs (max, PBS)=484 nm. The structure of Dye 12 is given below:

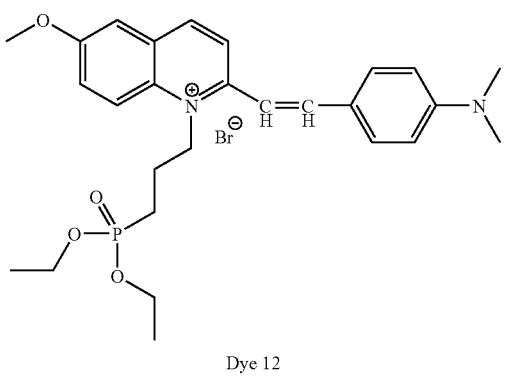

Dye 12

Example 13

Endoplasmic Reticulum Staining with Dye 1

Figure 1B:
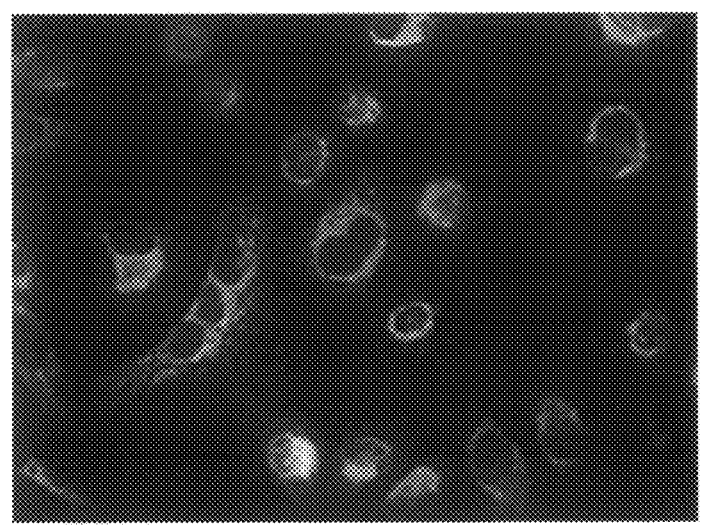

In this example, the endoplasmic reticulum (ER) of HeLa human cervical carcinoma cells were stained using Dye 1. HeLa cells were incubated with 20 µM of Dye 1 for 15 min at room temperature. As shown in FIG. 1, cells were imaged under bright field (top panel) and with a green channel (bottom panel).

Example 14

Mitochondrial Staining with Dye 2

Figure 2A:
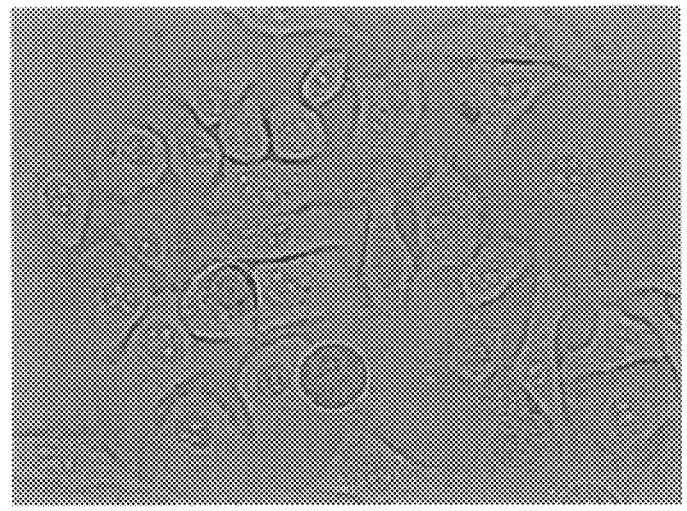
FIG. 2 are micrographs that show mitochondrial staining with Dye 2 of live HeLa human cervical carcinoma cells.
Figure 2B:
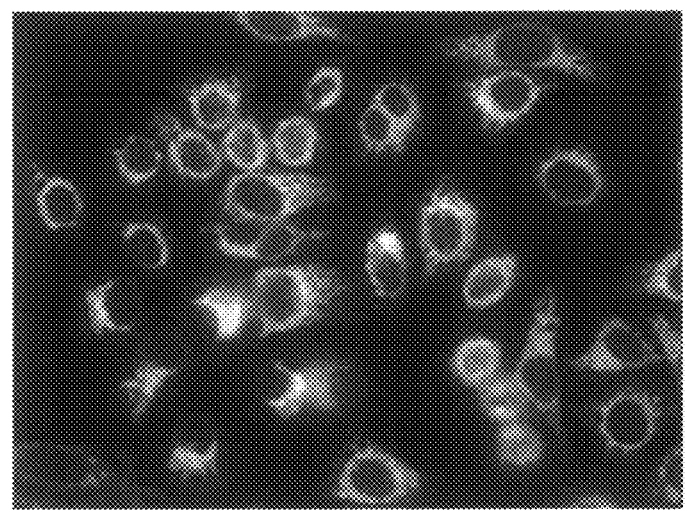

In this example, the mitochondria of live HeLa human cervical carcinoma cells were stained with Dye 2. As in the previous example, HeLa cells were incubated with 5 µM of Dye 2 for 15 min at room temperature. The results are shown in FIG. 2. Cells were imaged under bright field (top panel) and with a green FITC channel (bottom panel).

Example 15

Mitochondrial Staining with Dye 4

Figure 3A:
FIG. 3 are micrographs that show mitochondrial staining with Dye 4 of live HeLa human cervical carcinoma cells.
Figure 3B:
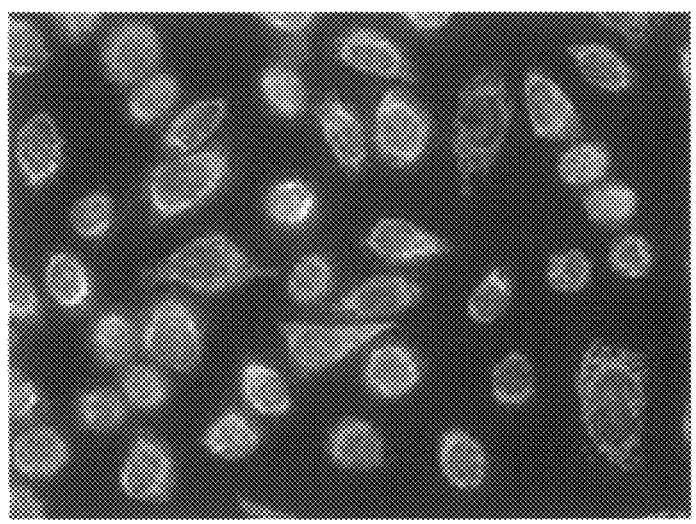

In this example, the mitochondria of live HeLa human cervical carcinoma cells were stained with Dye 4. HeLa cells were incubated with 10 µM of Dye 4 for 15 min at room temperature in a cover slip. The results of the staining are shown in FIG. 3. Cells were imaged under bright field (top panel) and with an orange channel (bottom panel).

Example 16

Endoplasmic Reticulum Staining with Dye 5

Figure 4A:
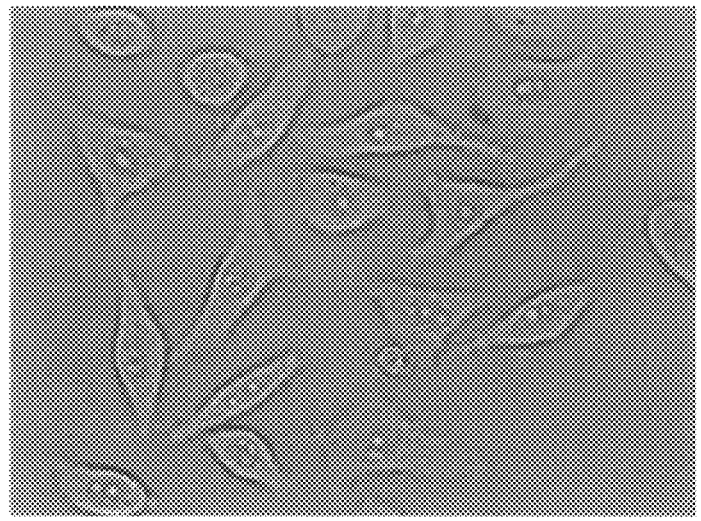
FIG. 4 are micrographs that show endoplasmic reticulum staining with Dye 5 of live HeLa human cervical carcinoma cells.
Figure 4B:
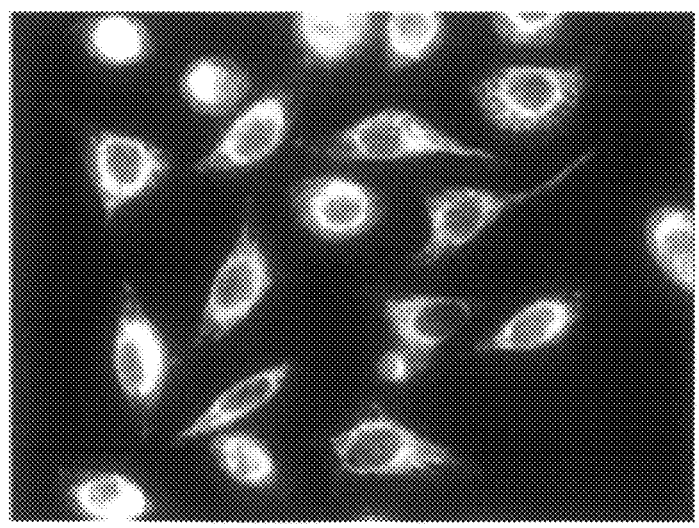

In this example, the ER of live HeLa human cervical carcinoma cells were stained with Dye 5. HeLa cells were incubated with 5 µM of Dye 5 for 15 min at room temperature. The results of the staining are shown in FIG. 4. Cells were imaged under bright field (top panel) and with a red channel (bottom panel).

Example 17

Whole Cell Staining with Dye 6

Figure 5A:
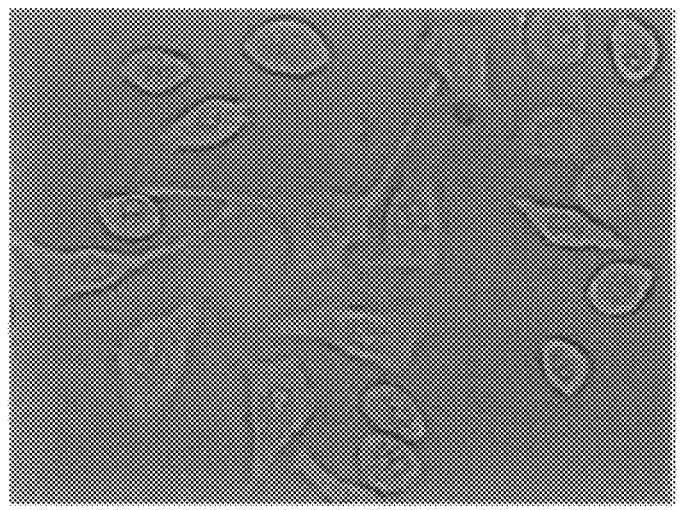
FIG. 5 are micrographs that show whole cell staining with Dye 6 of HeLa human cervical carcinoma cell line.
Figure 5B:
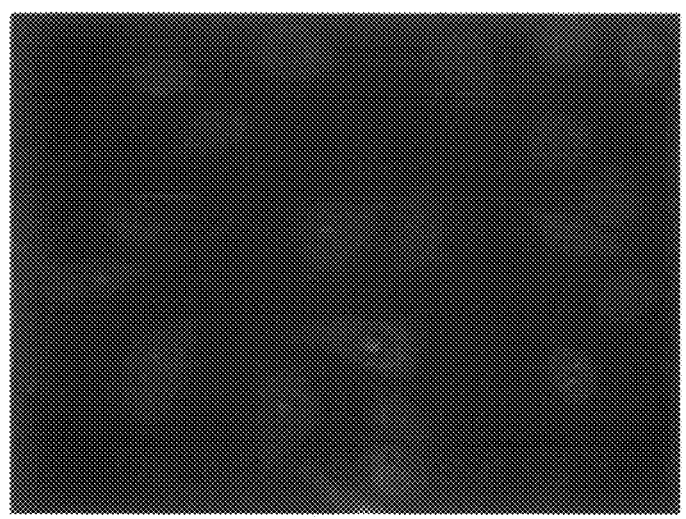

In this example, the total cells in HeLa human cervical carcinoma cell line were stained using Dye 6. HeLa cells were incubated with 40 µM of Dye 6 for 15 min at room temperature. The results of the staining are shown in FIG. 5. Cells were imaged under bright field (top panel) and with a red channel (bottom panel).

Example 18

Endoplasmic Reticulum Staining with Dye 7

Figure 6A:
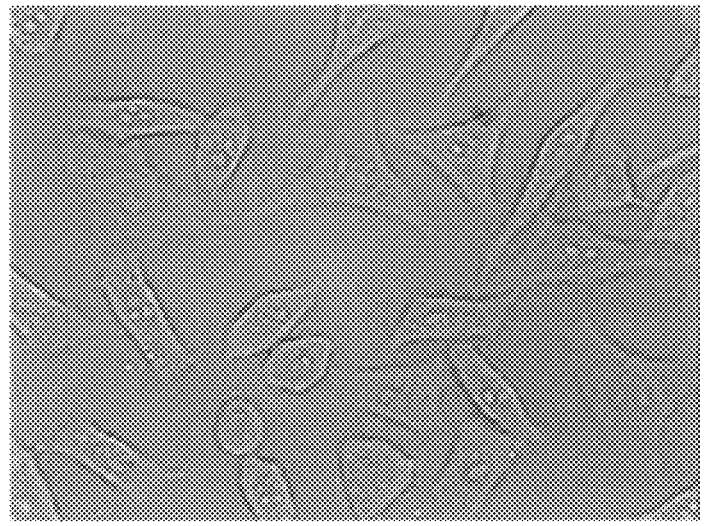
FIG. 6 are micrographs that show endoplasmic reticulum staining with Dye 7 of HeLa human cervical carcinoma cell line.
Figure 6B:
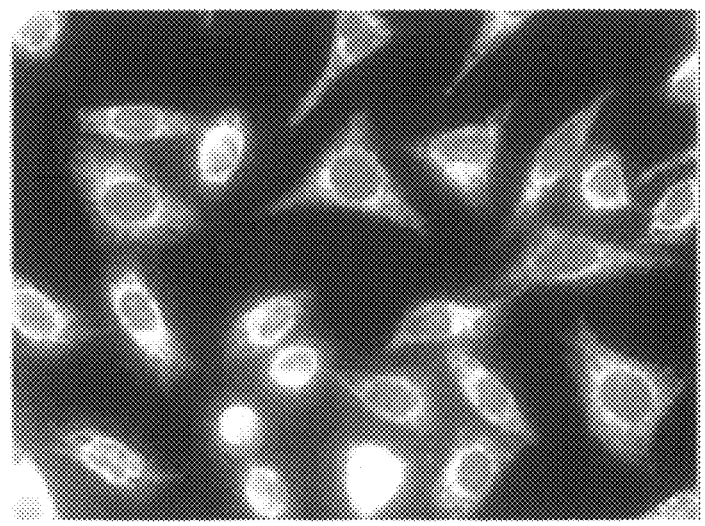

In this example, the ER of live HeLa human cervical carcinoma cells were stained with Dye 7. HeLa cells were incubated with 5 µM of Dye 7 for 15 min at room temperature. The results of the staining are shown in FIG. 6. Cells were imaged under bright field (top panel) and with a orange channel (bottom panel).

Example 19

Whole Cell Staining with Dye 8

Figure 7A:
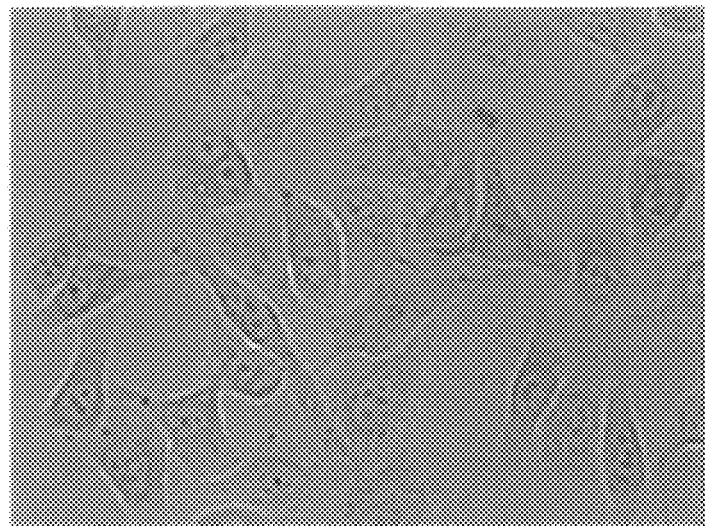
FIG. 7 are micrographs that show whole cell staining with Dye 8 of HeLa human cervical carcinoma cells.
Figure 7B:
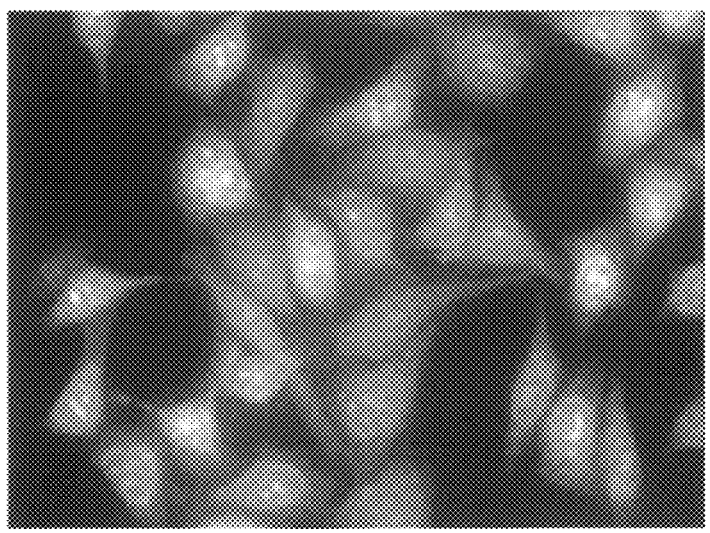

In this example, the whole cells in HeLa human cervical carcinoma cell line were stained using Dye 8. HeLa cells were incubated with 5 µM of Dye 8 for 15 min at room temperature. The results of the staining are shown in FIG. 7. Cells were imaged under bright field (top panel) and with a Cy5 channel (bottom panel).

Example 20

Mitochondrial Staining with Dye 9

Figure 8A:
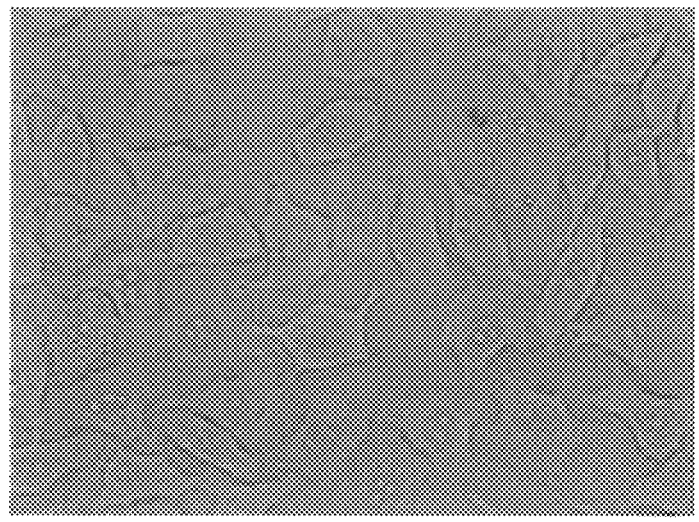
FIG. 8 are micrographs that show the staining with Dye 9 of the mitochondria of live HeLa human cervical carcinoma cells.
Figure 8B:
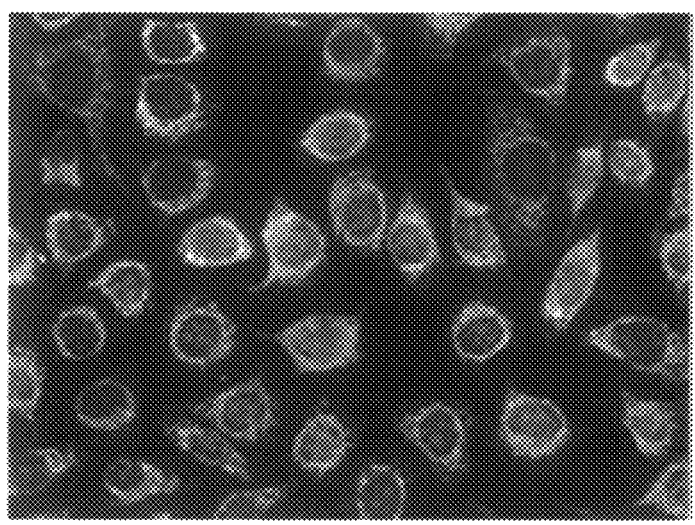

In this example, the mitochondria of live HeLa human cervical carcinoma cells were stained with Dye 9. HeLa cells were incubated with 1 µM of Dye 9 for 15 min at room temperature in a cover slip. The results of the staining are shown in FIG. 8. Cells were imaged under bright field (top panel) and with a red channel (bottom panel).

Example 21

Endoplasmic Reticulum Staining with Dye 10

Figure 9A:
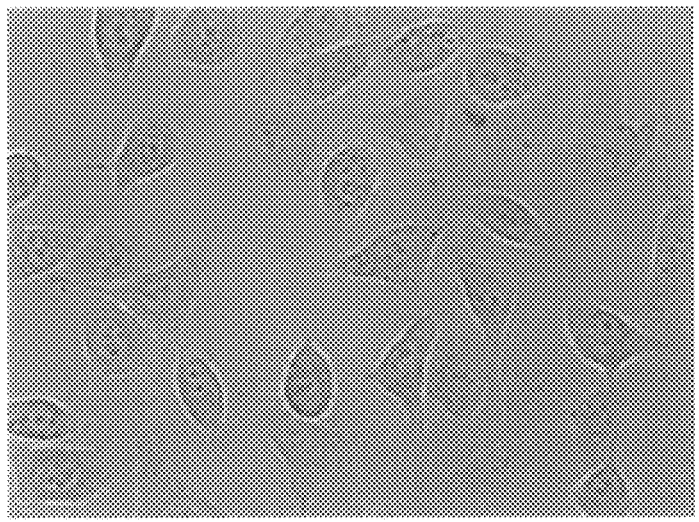
FIG. 9 are micrographs that show the staining with Dye 10 of endoplasmic reticulum of live HeLa human cervical carcinoma cells.
Figure 9B:
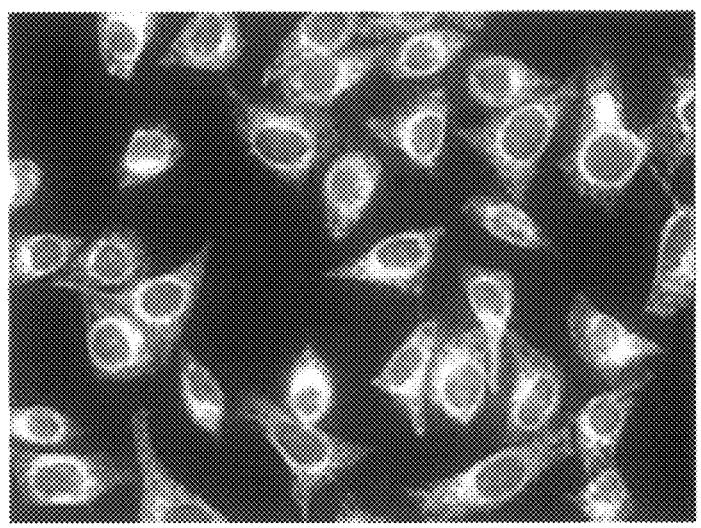

In this example, the ER of live HeLa human cervical carcinoma cells were stained with Dye 10. HeLa cells were incubated with 5 µM of Dye 10 for 15 min at room temperature. The results of the staining are shown in FIG. 9. Cells were imaged under bright field (top panel) and with an orange channel (bottom panel).

Example 22

Mitochondrial Staining with Dye 11

Figure 10A:
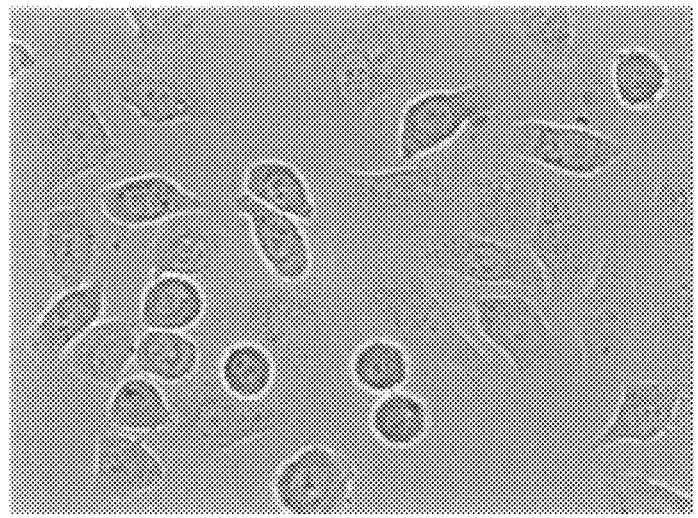
FIG. 10 are micrographs that show the staining with Dye 11 of mitochondria of live HeLa human cervical carcinoma cells.
Figure 10B:
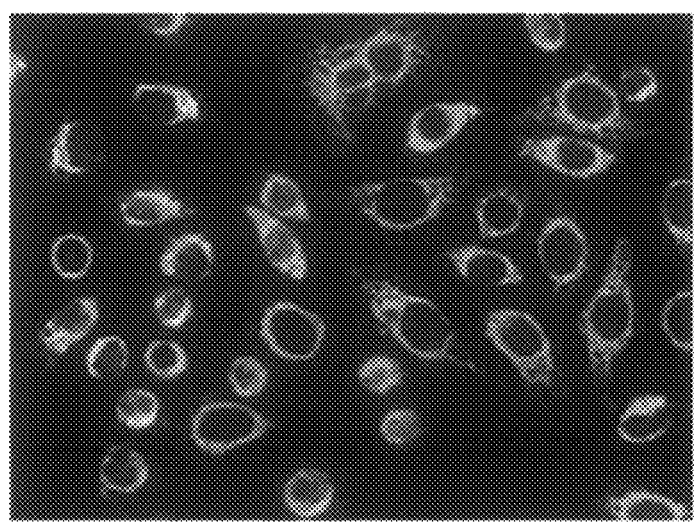

In this example, the mitochondria of live HeLa human cervical carcinoma cells were stained with Dye 11. HeLa cells were incubated with 5 µM of Dye 11 for 15 min at room temperature in a cover slip. The results of the staining are shown in FIG. 10. Cells were imaged under bright field (top panel) and with a green channel (bottom panel).

Example 23

Nucleoli Staining with Dye 12

Figure 11A:
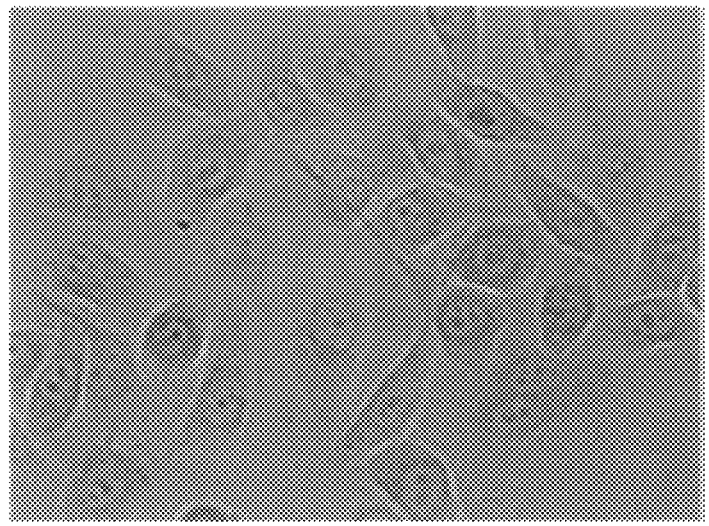
FIG. 11 are micrographs that show the staining with Dye 12 of mitochondria of live HeLa human cervical carcinoma cells.
Figure 11A:
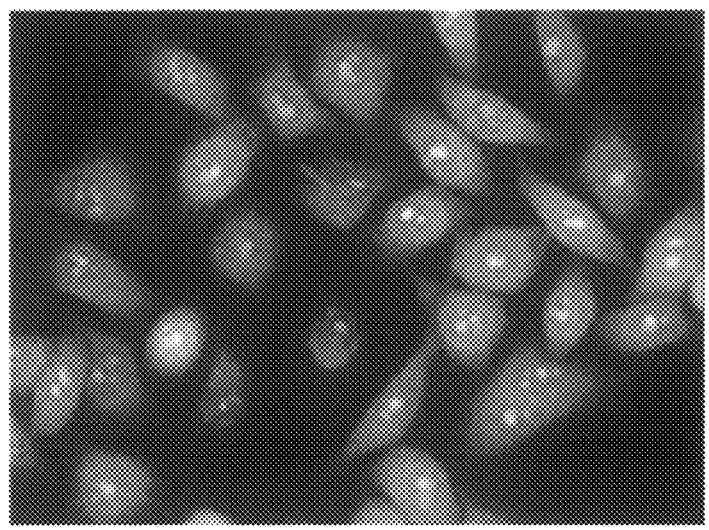

In this example, the nucleoli in HeLa human cervical carcinoma cell line were stained using Dye 12. HeLa cells were incubated with 5 µM of Dye 12 for 15 min at room temperature. The results of the staining are shown in FIG. 11. Cells were imaged under bright field (top panel) and with a red channel (bottom panel).

Many obvious variations will be suggested to those of ordinary skill in the art in light of the above detailed descriptions of the present invention. All such obvious variations are fully contemplated and are embraced by the scope and spirit of the present invention as set forth in the claims that now follow.

What is claimed is:

1. A compound having the structure:

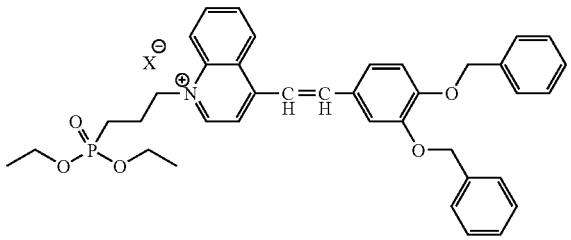 [SMILES: CCOP(=O)(CCC[n+]1ccc(C=Cc2ccc(OCc3ccccc3)c(OCc3ccccc3)c2)c2ccccc21)OCC]

wherein X comprises an anion.

2. A compound having the structure:

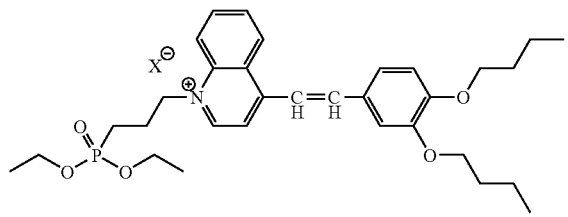 [SMILES: CCCCOc1ccc(C=Cc2cc[n+](CCCP(=O)(OCC)OCC)c3ccccc23)cc1OCCCC]

wherein X comprises an anion.

3. A compound having the structure:

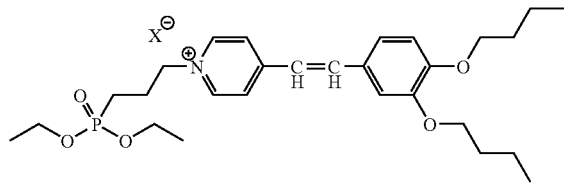 [SMILES: CCCCOc1ccc(C=Cc2cc[n+](CCCP(=O)(OCC)OCC)cc2)cc1OCCCC]

wherein X comprises an anion.

4. A compound having the structure:

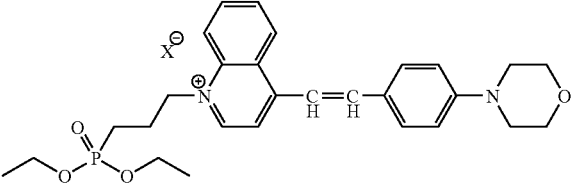 [SMILES: CCOP(=O)(CCC[n+]1ccc(C=Cc2ccc(N3CCOCC3)cc2)c2ccccc21)OCC]

wherein X comprises an anion.

5. A compound having the structure:

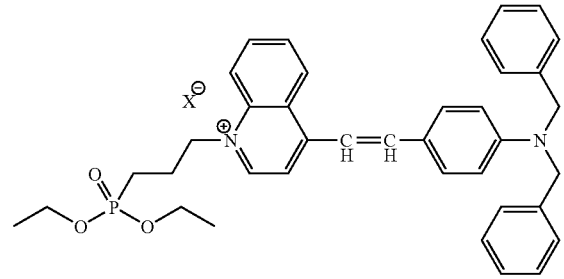 [SMILES: CCOP(=O)(CCC[n+]1ccc(C=Cc2ccc(N(Cc3ccccc3)Cc3ccccc3)cc2)c2ccccc21)OCC]

wherein X comprises an anion.

6. A compound having the structure:
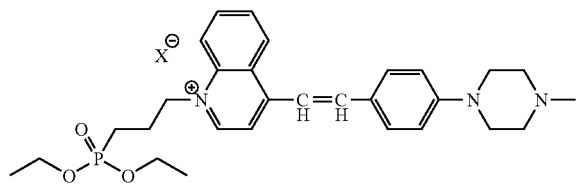 [SMILES: CCOP(=O)(CCC[n+]1ccc(C=Cc2ccc(N3CCN(C)CC3)cc2)c2ccccc21)OCC]
wherein X comprises an anion.
7. A compound having the structure:
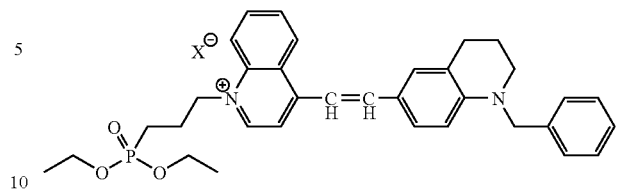
wherein X comprises an anion.
8. A compound having the structure:
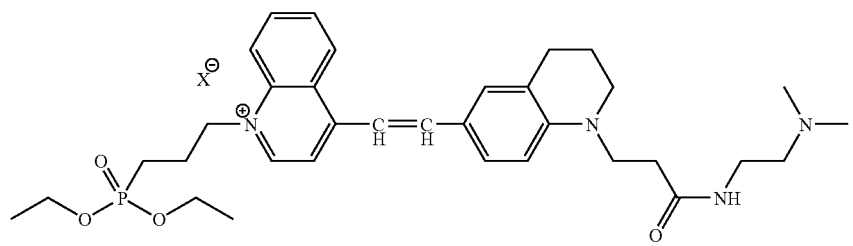 [SMILES: CCOP(=O)(CCC[n+]1ccc(C=Cc2ccc3c(c2)CCCN3CCC(=O)NCCN(C)C)c2ccccc21)OCC]
wherein X comprises an anion.
9. A compound having the structure:
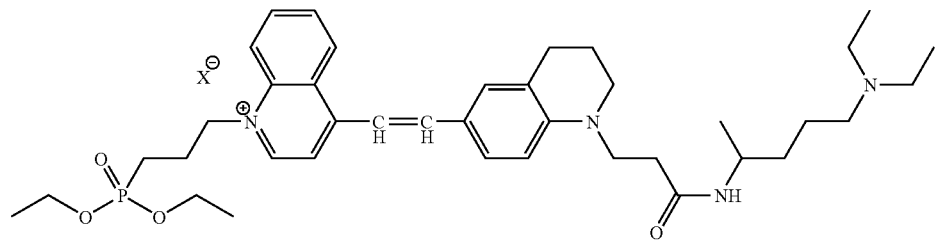 [SMILES: CCOP(=O)(CCC[n+]1ccc(C=Cc2ccc3c(c2)CCCN3CCC(=O)NC(C)CCCN(CC)CC)c2ccccc21)OCC]
wherein X comprises an anion.
10. A compound having the structure:
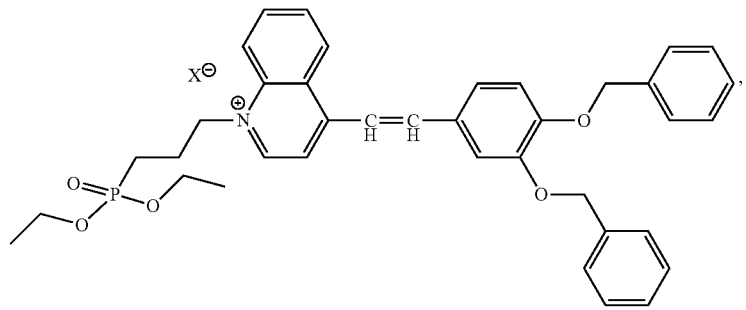
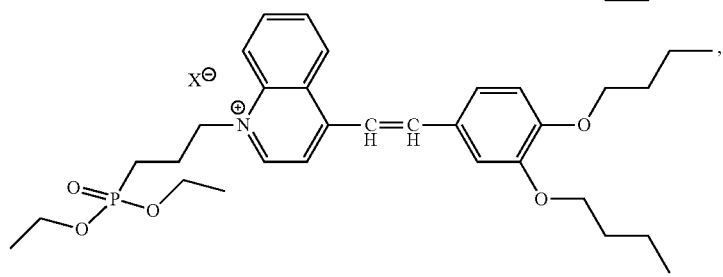

-continued
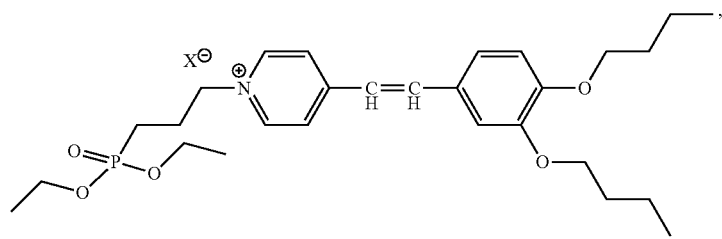
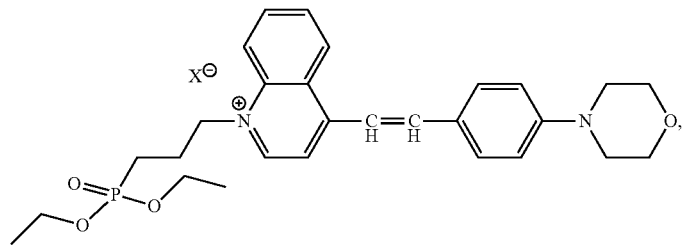
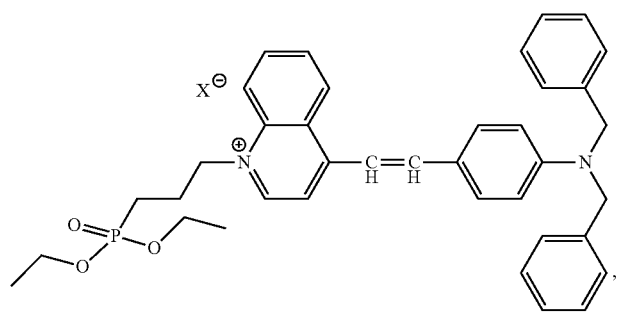
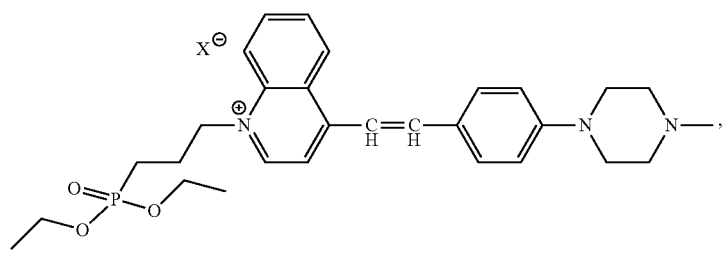
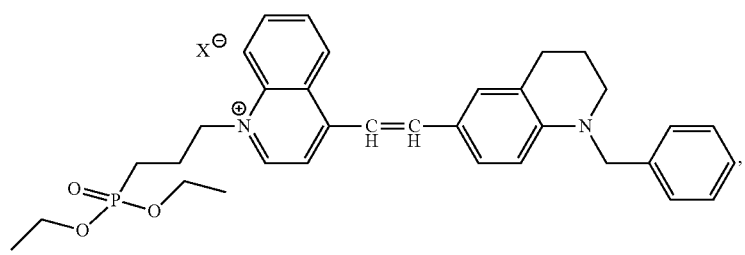
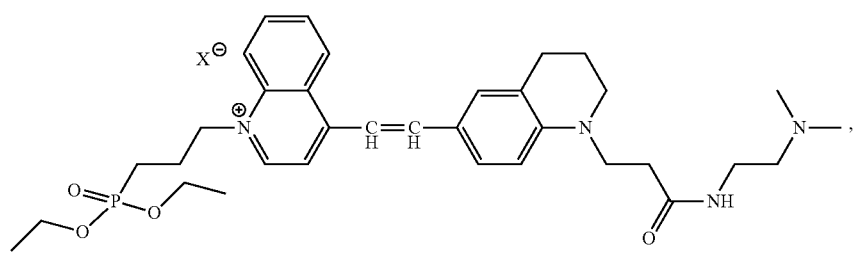

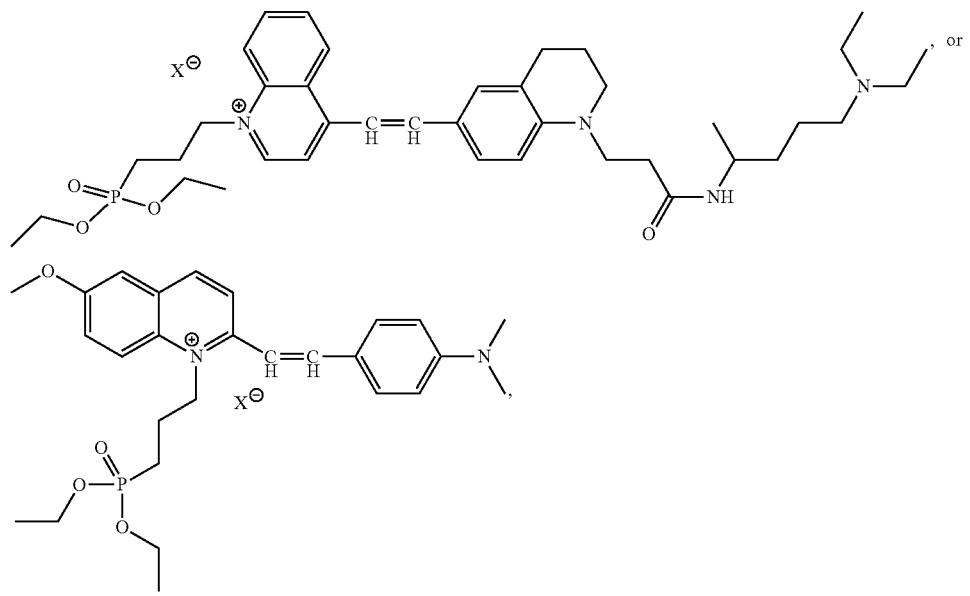
wherein X comprises an anion.
11. A compound having the structure:
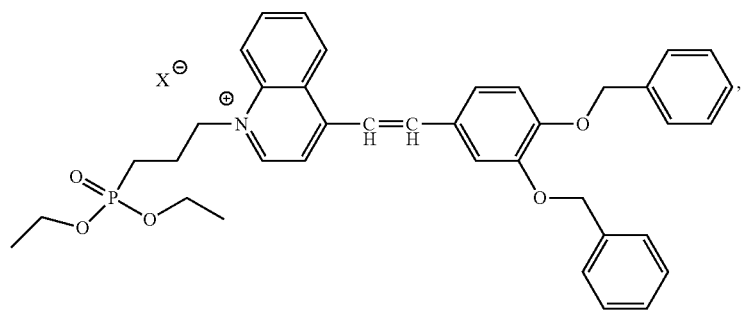
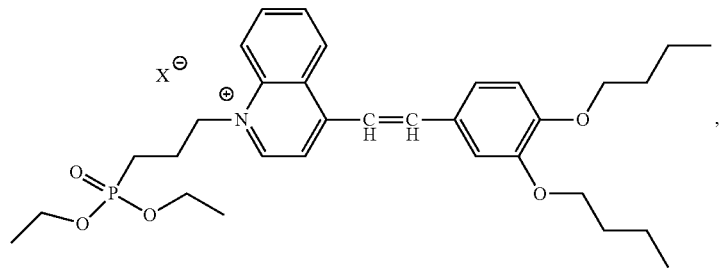
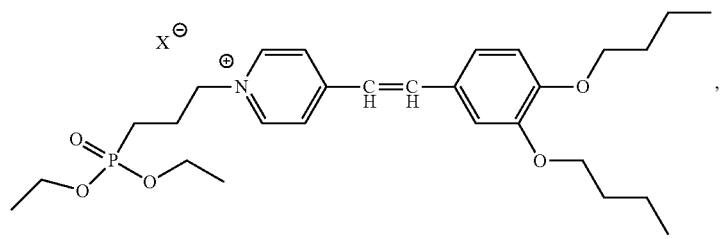

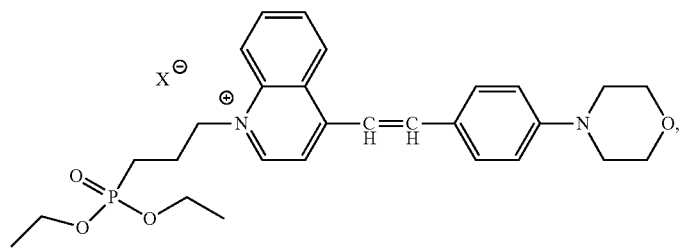
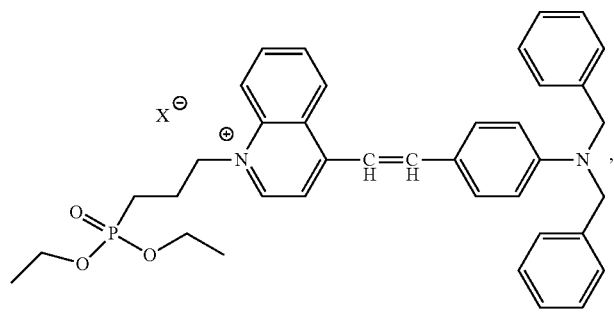
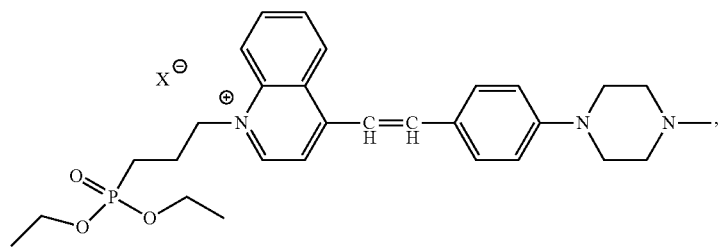
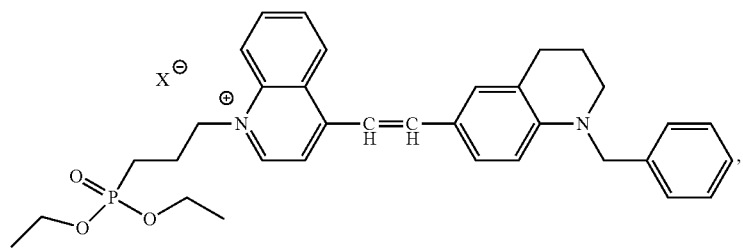
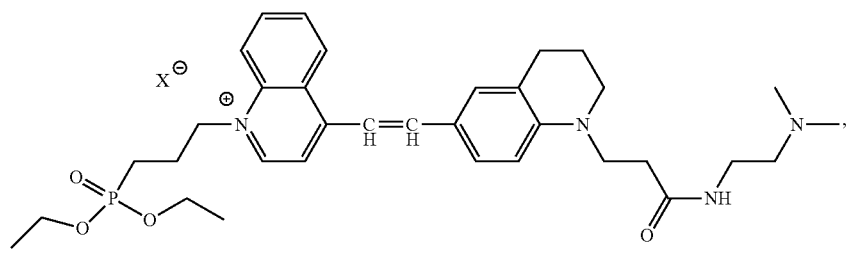
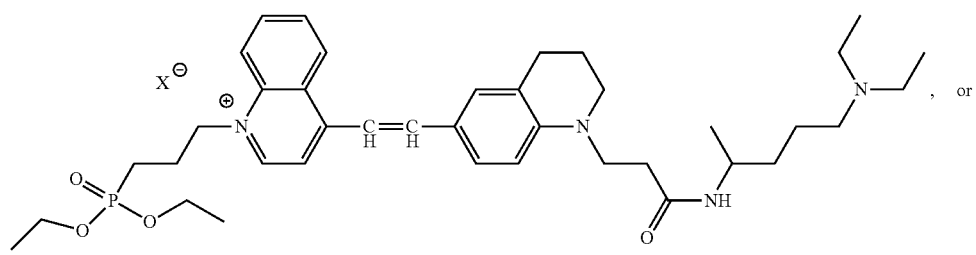

-continued

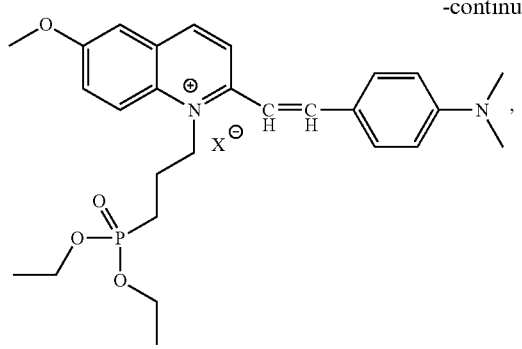

wherein X comprises an anion and wherein the compound also has at least one reactive group.

12. A compound having the structure:

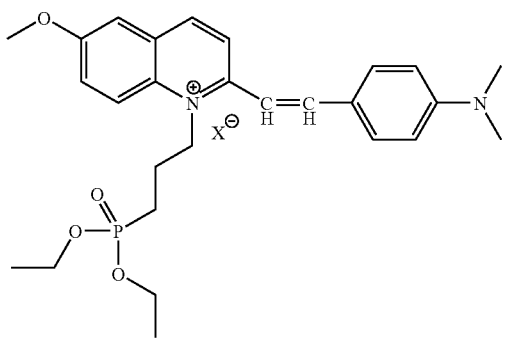

wherein X comprises an anion.

13. A method of labeling a target molecule comprising the steps of:
(a) providing:
(i) a sample containing said target molecule; and
(ii) the compound of claim 11; and
(b) attaching said compound by means of said reactive group to said target molecule in the sample, thereby labeling said target molecule.

14. The compound of claim 11, wherein said reactive group comprises a nucleophilic reactive group, an electrophilic reactive group, a terminal alkene, a terminal alkyne, a coordinate group or an alkylating agent.

15. The compound of claim 11, wherein said reactive group is a nucleophilic reactive group that comprises a thiol, amine or hydroxyl group.

16. The compound of claim 11, wherein said reactive group is an electrophilic reactive group that comprises an isocyanate, isothiocyanate, monochlorotriazine, dichlorotriazine, 4,6,-dichloro-1,3,5-triazines, mono- or di-halogen substituted pyridine, mono- or di-halogen substituted diazine, maleimide, haloacetamide, aziridine, sulfonyl halide, acid halide, hydroxysuccinimide ester, hydroxysulfosuccinimide ester, imido ester, hydrazine, azidonitrophenol, azide, 3-(2-pyridyl dithio)-proprionamide, glyoxal or aldehyde group.

17. A method of identifying a specific organelle or region in a cell of interest comprising the steps of:
(A) providing
(i) said cell of interest; and
(ii) the compound of claim 10, wherein the compound stains the specific organelle or region;
(B) incubating said cell of interest with said compound; and
(C) identifying the location or said organelle or region in the cell of interest by identifying the compound that stains said organelle or region.

18. The method of claim 17, wherein said compound is

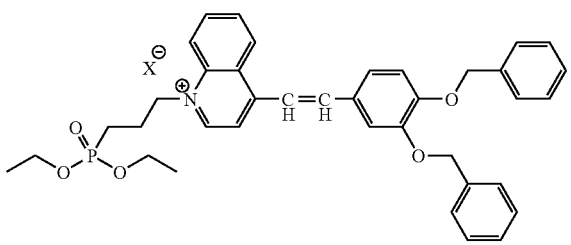 [SMILES: CCOP(=O)(CCC[n+]1ccc(C=Cc2ccc(OCc3ccccc3)c(OCc3ccccc3)c2)c2ccccc21)OCC]

wherein X comprises an anion, and said organelle or region is endoplasmic reticulum.

19. The method of claim 17, wherein said compound is

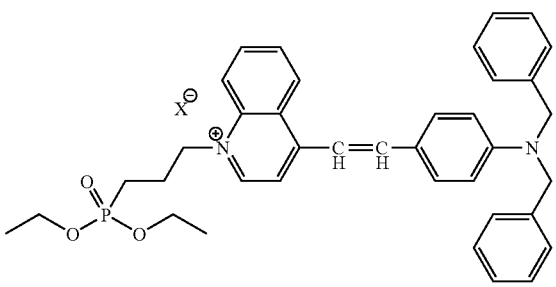 [SMILES: CCOP(=O)(CCC[n+]1ccc(C=Cc2ccc(N(Cc3ccccc3)Cc3ccccc3)cc2)c2ccccc21)OCC]

wherein X comprises an anion, and said organelle or region is endoplasmic reticulum.

20. The method of claim 17, wherein said compound is

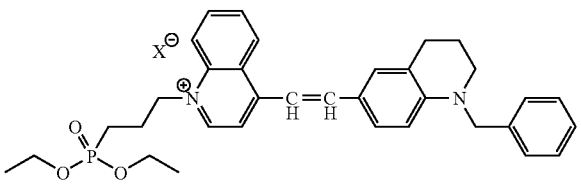 [SMILES: CCOP(=O)(CCC[n+]1ccc(C=Cc2ccc3c(c2)CCCN3Cc2ccccc2)c2ccccc21)OCC]

wherein X comprises an anion, and said organelle or region is endoplasmic reticulum.

21. The method of claim 17, wherein said compound is

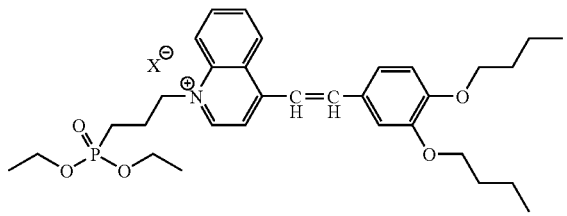 [SMILES: CCCCOc1ccc(C=Cc2cc[n+](CCCP(=O)(OCC)OCC)c3ccccc23)cc1OCCCC]

wherein X comprises an anion, and said organelle or region is a mitochondrion.

22. The method of claim 17, wherein said compound is

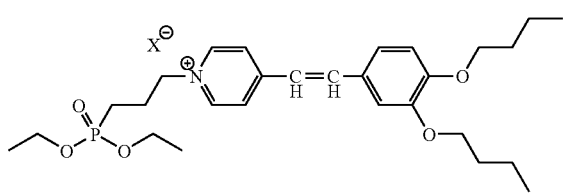 [SMILES: CCCCOc1ccc(C=Cc2cc[n+](CCCP(=O)(OCC)OCC)cc2)cc1OCCCC]

wherein X comprises an anion, and said organelle or region is a mitochondrion.

23. The method of claim 17, wherein said compound is

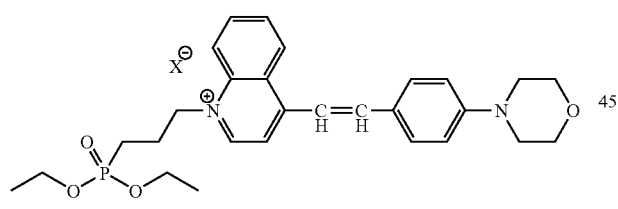

wherein X comprises an anion, and said organelle or region is a mitochondrion.

24. The method of claim 17, wherein said compound is

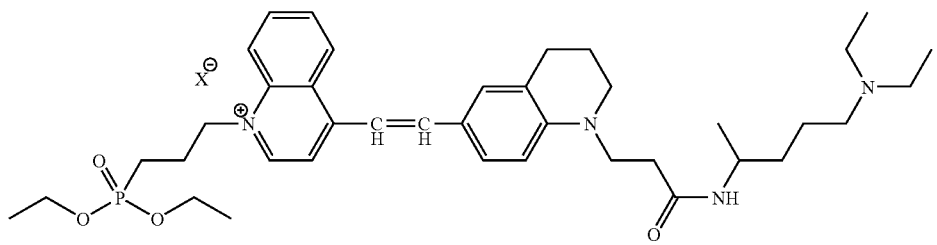 [SMILES: CCOP(=O)(CCC[n+]1ccc(C=Cc2ccc3c(c2)CCCN3CCC(=O)NC(C)CCCN(CC)CC)c2ccccc21)OCC]

wherein X comprises an anion, and said organelle or region is a mitochondrion.

25. The method of claim 17, wherein said compound is

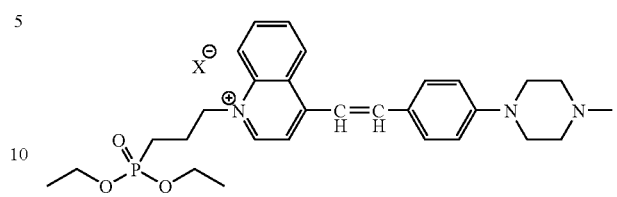

wherein X comprises an anion, and said organelle or region is the whole cell.

26. The method of claim 17, wherein said compound is

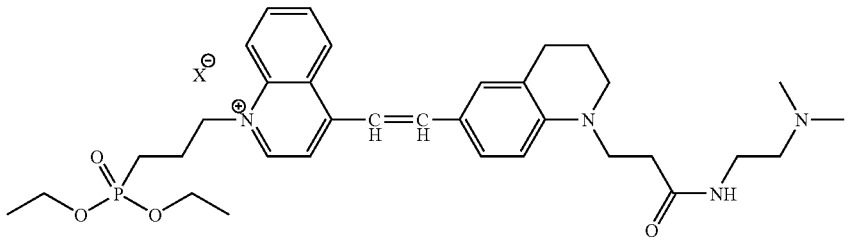 [SMILES: CCOP(=O)(CCC[n+]1ccc(C=Cc2ccc3c(c2)CCCN3CCC(=O)NCCN(C)C)c2ccccc21)OCC]

wherein X comprises an anion, and said organelle or region is the whole cell.

27. The method of claim 17, wherein compound is

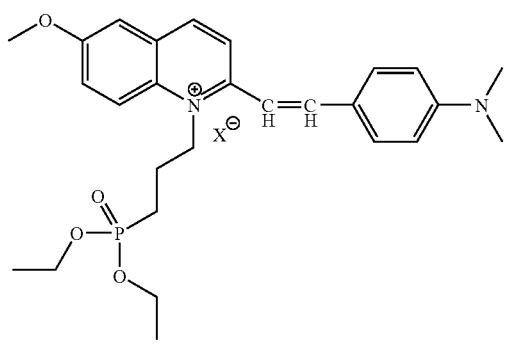

wherein X comprises an anion, and said organelle or region is a nucleolus.

28. A kit for identifying an organelle or region in a cell of interest or in a sample containing a cell of interest, said kit comprising in packaged combination:
(A) the compound of claim 10;
(B) optional buffers; and (C) instructions or a protocol for recommended use of the kit.

29. A target molecule comprising the compound of claim 10.

30. The target molecule of claim 29, wherein the target molecule is a nucleoside, a nucleotide, an oligonucleotide, a polynucleotide, a peptide nucleic acid, a protein, an oligopeptide, an enzyme, an antibody, a cytokine, avidin, streptavidin, digoxigenin, an oligosaccharide, a polysaccharide, a lipid, a liposome, a glycolipid, or a dye.

31. The target molecule of claim 29, wherein the target molecule is a protein, an oligopeptide, a nucleotide, an oligonucleotide, or a polynucleotide.

32. The method of claim 13, wherein the target molecule is a nucleoside, a nucleotide, an oligonucleotide, a polynucleotide, a peptide nucleic acid, a protein, a peptide, an enzyme, an antibody, a cytokine, avidin, streptavidin, digoxigenin, an oligosaccharide, a polysaccharide, a lipid, a liposome, a glycolipid, or a dye.

33. The method of claim 13, wherein the target molecule is a protein, a peptide, a nucleotide, an oligonucleotide, or a polynucleotide.

\* \* \* \* \*